US007754220B2

(12) United States Patent
Ohtaki et al.

(10) Patent No.: US 7,754,220 B2
(45) Date of Patent: Jul. 13, 2010

(54) METHODS OF INHIBITING SECRETION OF FOLLICLE-STIMULATING HORMONE AND TESTOSTERONE

(75) Inventors: Tetsuya Ohtaki, Ibaraki (JP); Hisanori Matsui, Ibaraki (JP); Hirokazu Matsumoto, Ibaraki (JP); Chieko Kitada, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/547,974

(22) PCT Filed: Mar. 11, 2004

(86) PCT No.: PCT/JP2004/003226

§ 371 (c)(1),
(2), (4) Date: May 4, 2006

(87) PCT Pub. No.: WO2004/080479

PCT Pub. Date: Sep. 23, 2004

(65) Prior Publication Data

US 2006/0287227 A1 Dec. 21, 2006

(30) Foreign Application Priority Data

Mar. 12, 2003 (JP) ............................. 2003-067283
Sep. 3, 2003 (JP) ............................. 2003-311892

(51) Int. Cl.
A61K 38/16 (2006.01)
A61K 38/17 (2006.01)

(52) U.S. Cl. ........................................ 424/198.1; 514/12

(58) Field of Classification Search ....................... None
See application file for complete search history.

(56) References Cited

U.S. PATENT DOCUMENTS

| 6,699,965 | B1 * | 3/2004 | Watanabe et al. ............ 530/300 |
| 2003/0096956 | A1 | 5/2003 | Suenaga et al. |
| 2004/0185525 | A1 | 9/2004 | Nishimura et al. |
| 2004/0236077 | A1 | 11/2004 | Matsumoto et al. |
| 2005/0176091 | A1 | 8/2005 | Yamada et al. |
| 2006/0241051 | A1 * | 10/2006 | Kitada et al. ............... 514/15 |
| 2006/0287227 | A1 | 12/2006 | Ohtaki et al. |

FOREIGN PATENT DOCUMENTS

| EP | 0 162 575 A2 | 11/1985 |
| EP | 1126028 | 8/2001 |
| EP | 1577323 | 9/2005 |
| JP | 9-169735 | 6/1997 |
| JP | 2002-320496 | 11/2002 |
| JP | 2003-26601 | 1/2003 |
| JP | 2003-300906 | 10/2003 |
| JP | 2004-217651 | 8/2004 |
| WO | WO-97/40071 | 10/1997 |
| WO | WO-98/39448 | 9/1998 |
| WO | WO 00/24890 | 5/2000 |
| WO | WO-01/44469 A1 | 6/2001 |
| WO | 01/74377 | 10/2001 |
| WO | WO 01/75104 A1 | 10/2001 |
| WO | WO 02/085399 A1 | 10/2002 |
| WO | WO-02/092829 A1 | 11/2002 |
| WO | WO-03/027149 A1 | 4/2003 |
| WO | WO-03/060125 A1 | 7/2003 |
| WO | WO-2004/038021 A1 | 5/2004 |
| WO | 2004/060264 A2 * | 7/2004 |
| WO | WO-2004/060264 A2 | 7/2004 |
| WO | WO-2004/063221 A1 | 7/2004 |
| WO | WO-2004/080479 A1 | 9/2004 |
| WO | WO-2004/087622 A2 | 10/2004 |
| WO | WO-2004/096855 A2 | 11/2004 |
| WO | WO-2004/101747 A2 | 11/2004 |
| WO | WO-2004/106289 A1 | 12/2004 |
| WO | WO-2005/095973 A2 | 10/2005 |
| WO | WO-2006/001499 A2 | 1/2006 |
| WO | WO-2007/072997 A1 | 6/2007 |
| WO | WO-2007/084211 A2 | 7/2007 |

OTHER PUBLICATIONS

Tomita et al, Bioorganic & Med. Chem. 14:7595-7603, 2006.*
Kotani et al, J. Biol. Chem. 276(37):34631-34636, 2001.*
Cleland et al, April, Current Opinion in Biotechnology 12: 212-219, 2001.*
Rudinger in J.A. Parsons, ed. "Peptide hormones", University Park Press, 1976.*
Ngo et al., In Merz et al., ed. "The protein folding problem and tertiary structure prediction", Birkhauser, 1994.*
Evans et al, J. Endocrinol. 145(1):113-119, 1995; Abstract only.*
Homburg et al, British Med. J. 298(6676):809-812, 1989.*
Andreyko et al, Obstet. Gynecol. Surv. 42(1):1-21, 1987; Abstract only.*
A. Dutta et al., "Polypeptides, Part 15. Synthesis and Biological Activity of α-Aza-analogues of Luliberin modified in Positions 6 and 10", *Journal of the Chemical Society*, Perkin Transactions I, No. 2, pp. 379-388 (1979).
T. Ohtaki et al., "Metastasis Suppressor Gene KiSS-1 Encodes Peptide Ligand of a G-Protein-Coupled Receptor", *Nature*, vol. 411, pp. 613-617 (2001).
M. Kotani et al., "The Metastasis Supressor Gene KiSS-1 Enclodes Kisspeptins, the Natural Ligands of the Orphan G Protein-Coupled Receptor GPR54", *The Journal of Biological Chemistry*, vol. 276: No. 37, pp. 34631-34636 (2001).
M. Ringel et al., "Metastin Receptor is Overexpressed in Paillary Thyroid Cancer and Activates MAP Kinase in Thyroid Cancer Cells", *The Journal of Clinical Endocrinology & Metabolism*, 87(5): 2399-2402 (2002).

(Continued)

Primary Examiner—Ruixiang Li
(74) Attorney, Agent, or Firm—David G. Conlin; Colleen J. McKiernan; Edwards Angell Palmer & Dodge LLP

(57) ABSTRACT

Metastin, compounds that promote the activity of metastin or its receptors and the like are excellent gonadal function improving agents, ovulation inducers or promoters, gonadotropic hormone secretion promoters, gonadotropic hormone secretion inhibitors, sex hormone secretion promoters, sex hormone secretion inhibitors, etc., and can be used as agents for preventing/treating sterility, hormone-sensitive cancers, endometriosis, etc. Metastin and its receptors are useful for screening for these pharmaceuticals.

2 Claims, 12 Drawing Sheets

OTHER PUBLICATIONS

S. Han et al., "Orphan G Protein-Coupled Receptors MrgA1 and MrgC11 are Distinctively Activated by RF-amide-related Peptides Through the $G\alpha_{q/11}$ Pathway", *PNAS*, vol. 99, No. 23, pp. 14740-14745 (2002).

A. Niita et al., "Genome Information Convergent Type of Drug Development Research: Depolymerization of the Cancer Metastasis Suppressor Gene, KiSS-1 (Metastin)", Yuki 2B-13-2, 53$^{rd}$, Nihon Yakugaku kai, Kinki Shibu Sokai, Taikai, Koen Yoshi-shu (2003).

T. Masui et al., "Metastin and Its Variant Forms Suppress Migration of Pancreatic Cancer Cells", *Biochemical and Biophysical Resaerch Communications*, 315, pp. 85-92 (2004).

Y. Terao et al., "Express of KiSS-1, a Metastasis Suppressor Gene, in Trophoblast Giant Cells of the Rat Placenta", *Biochimica et Biophysica Acta*, 1678, pp. 102-110 (2004).

M.L. Gottsch et al., "A Role for Kisspeptins in the Regulation of Gonadotropin Secretion in the Mouse", *Endocrinology*, 145(9), pp. 4073-4077 (2004).

Niida et al., "Design and synthesis of downsized metastin (45-54) analogs with maintenance of high GPR54 agonistic activity," Bioorganic & Medicinal Chemistry Letters (2006) 16:134-137.

Tomita et al., "Structure-activity relationship study on small peptidic GPR54 agonists," Bioorganic & Medicinal Chemistry (2006) 14:7595-7603.

Venkatesan et al., "Synthesis and Enzyme Inhibitory Activities of Novel Peptide Isosteres," Current Medicinal Chemistry (2002) 9:2243-2270.

Muir et al., "AXOR12, a Novel Human G Protein-coupled Receptor, Activated by the Peptide KiSS-1," Journal of Biological Chemistry (2001), 276(31):28969-28975.

Supplementary European Search Report for corresponding European application EP04719659, dated May 26, 2009.

The Journal of Clinical Endocrinology & Metabolism, "Dramatic Elevation of Plasma Metastin Concentrations in Human Pregnancy: Metastin as a Novel Plascenta-Derived Hormone in Humans," 88(2):914-919 (2003).

* cited by examiner

METHODS OF INHIBITING SECRETION OF FOLLICLE-STIMULATING HORMONE AND TESTOSTERONE

FIELD OF THE INVENTION

The present invention relates to gonadal function improving agents. More particularly, the present invention relates to agents for preventing/treating sterility, ovulation inducers or promoters, gonadotropin secretion promoters or inhibitors, sex hormone secretion promoters or inhibitors, agents for preventing/treating hormone-sensitive cancers, and screening for these agents, diagnosis for sterility, and so on.

BACKGROUND ART

Increased rates of infertility accompanied by the delay in age at marriage and declining birthrates have been global problems in advanced countries of the day. It is likely that interest in sterility treatment will continue to grow more and more in the future.

Treatment of sterility due to disorders of ovulation in women involves stimulation of follicular development by recombinant FSH (follicle stimulating hormone) or human menopausal gonadotropins (hMG preparations), induction of ovulation by human chorionic gonadotropins (hCG), and the like. Artificial insemination has also frequently been used, and superovulation treatment through hMG-hCG therapy has been applied widely. In the normal menstrual cycle, luteinizing hormone (LH) surged up from the pituitary is received on LH receptors in mature follicular granulosa cells, whereby ovulation is induced. The hCG described above is based on the mimicry of this endogenous LH surge, and stimulation of LH receptors by hCG in lieu of LH is the mechanism of inducing ovulation. In addition, production techniques for recombinant human LH (rhLH) was developed recently, and ovulation induction treatment with rhLH has also started (J. Clin. Endocrinol. Metab., 86, 2607-2618, 2001). In the ovary which receives LH, the expression of many genes is induced, which subsequently leads to ovulation. What is directly involved in ovulation phenomenon is a gene product induced by LH, rather than LH itself. It is reported that when downstream genes for LH such as progesterone receptor or cyclooxygenase-2 are knocked out, ovulation is inhibited (reviews: Steroids, 65, 559-570, 2000; Endocrinology, 143, 2823-2835, 2002). With expanding hMG-hCG therapy, patients with developed complications increased, which has become a clinically serious problem. One of the highest incidences of complications is ovarian hyperstimulation syndrome (OHSS). OHSS is an iatrogenic disorder and is onset by administration of hMG or hCG or overproduction of hCG in mother body after conception. In its severe form, ovarian enlargement and ascites occur, and may be even life-threatening for patients. For this reason, there are a variety of diagnostic techniques for preventing OHSS in the clinical phase. When blood estrogen shows a high level, or when polycystic ovaries are observed by ultrasound scanning, measures to discontinue ovulation induction, etc. are taken (Acta Obstet. Gynecol. Scand. 80, 878-882, 2001).

For sterility having causes relating to the man, medical or surgical treatment is available when physical factors such as varicoceles or seminal tract obstruction, etc. are found. However, when its causes are found in reproductive functions such as disorder of sperm producing function, ejaculatory dysfunction, etc., any effective treatment has hardly been established.

Gonadotropins (gonad-stimulating hormone) such as FSH, LH, etc., which are released from the pituitary are largely involved in maturation of ova or sperm and stimulate the secretion of estrogen and progesterone from the ovaries. Release of these gonadotropins is induced by GnRH (gonadotropin-releasing hormone) secreted from the hypothalamus. Normally, GnRH is released intermittently so that FSH and LH are released at certain intervals. Pulsatile release of GnRH is crucial for maintenance of gonadotropins in blood to a certain level and continuous administration of GnRH conversely results in decreased level of gonadotropins in blood (Science, 202, 631-633, 1978). FSH and LH released pulsatile stimulate maturation of the ovum and sperm in the ovary and testicle, respectively, synthesis of sex hormones, and the like. The pulsatile release of GnRH and gonadotropins also takes part in development of reproductive organs in childhood and maturation of the reproductive organs during adolescence. In addition, ovulation is induced by an LH and FSH surge immediately before ovulation, and reportedly GnRH is surged strongly also in this occasion. As such, GnRH and gonadotropins are important factors for supporting reproductive functions in both female and male individuals and abnormalities in these functions are reflected as reproductive abnormalities involving infertility mainly (Endocrinology, 143, 2823-2835, 2002).

On the other hand, human metastin (human KiSS-1 peptide) is a peptide consisting of 54 amino acids, purified from human placenta and was found to be the ligand for a G-protein-coupled human OT7T175 (WO 00/24890). Rat type (rat metastin) and mouse type (mouse metastin) of human metastin are also reported (WO 01/75104). Metastin has a cancer metastasis inhibiting activity and is useful for the prevention/treatment of cancers (e.g., lung cancer, gastric cancer, liver cancer, pancreatic cancer, colorectal cancer, rectal cancer, colon cancer, prostate cancer, ovarian cancer, cervical cancer, breast cancer, kidney cancer, bladder cancer, brain tumor, etc.); metastin has a pancreatic function regulating action and is useful for the prevention/treatment of pancreatic diseases (e.g., acute or chronic pancreatitis, pancreatic cancer, etc.), and metastin has a placenta function regulating action and is useful for the prevention/treatment of choriocarcinoma, hydatid moles, invasive moles, miscarriage, fetal hypoplasia, sugar dysbolism, lipid dysbolism or abnormal delivery (WO 00/24890, WO 01/75104, etc.). Furthermore, sustained preparations containing metastin are reported (WO 02/85399). Recently, it is reported that the metastin level in blood from pregnant women rapidly rises with initiation of pregnancy and its expression is maintained at a high level until delivery (J. Clin. Endocrinol Metab., 88, 914-919, 2003).

Since the actual mechanism for the onset of OHSS remains elusive, women with severe infertility should be given hMG-hCG therapy, etc., OHSS is considered an unavoidable disease in the current fertility treatment. It has been desired to develop ovulation inducers having an ovulation-promoting effect comparable to conventional ovulation inducers represented by hCG without causing OHSS. It has also been desired to develop drugs effective for male infertility.

DISCLOSURE OF INVENTION

Under the present circumstances, the present inventors made extensive investigations and have thus found that human metastin has a gonadotropin release-promoting effect, a gonadal function improving effect, an ovulation promoting effect, etc. The inventors have further clarified that ovulation by metastin is a phenomenon of ovulation mediated by normal differentiation of estrogen-producing granulosa cells into progesterone-producing luteal cells, and continuous administration of metastin reduces the release of gonadotropins and production of testosterone in the testis. As a result of further studies, the inventors have come to accomplish the present invention.

More specifically, the present invention relates to the following features, and so on.

(1) A gonadal function improving agent, which comprises a polypeptide comprising the same or substantially the same amino acid sequence as the amino acid sequence represented by SEQ ID NO: 1, or a salt thereof.

(2) The gonadal function improving agent according to (1), which comprises a polypeptide consisting of the amino acid sequence represented by SEQ ID NO: 3, or a salt thereof.

(2a) The gonadal function improving agent according to (1), which comprises a polypeptide consisting of the amino acid sequence represented by SEQ ID NO: 9, SEQ ID NO: 11, SEQ ID NO: 13 or SEQ ID NO: 15, or a salt thereof.

(3) The gonadal function improving agent according to (1), wherein the amino acid sequence which is substantially the same as the amino acid sequence represented by SEQ ID NO: 1 is the amino acid sequence represented by SEQ ID NO: 2.

(3a) The gonadal function improving agent according to (1), which comprises a polypeptide consisting of the amino acid sequence represented by SEQ ID NO: 5, or a salt thereof.

(3b) The gonadal function improving agent according to (1), which comprises a polypeptide consisting of the amino acid sequence represented by SEQ ID NO: 7, or a salt thereof.

(4) A gonadal function improving agent, which comprises a polynucleotide encoding a polypeptide comprising the same or substantially the same amino acid sequence as the amino acid sequence represented by SEQ ID NO: 1, or a salt thereof.

(4a) A gonadal function improving agent, which comprises a polynucleotide consisting of the base sequence represented by SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 17, SEQ ID NO: 18 or SEQ ID NO: 19.

(5) A gonadal function improving agent, which comprises a compound or its salt that promotes the activity of a polypeptide comprising the same or substantially the same amino acid sequence as the amino acid sequence represented by SEQ ID NO: 1, or a salt thereof.

(5a) The gonadal function improving agent according to (5), wherein the compound is a compound that promotes the activity of a polypeptide consisting of the amino acid sequence represented by SEQ ID NO: 3, or a salt thereof.

(6) A gonadal function improving agent, which comprises a compound or its salt that promotes the activity of a protein comprising the same or substantially the same amino acid sequence as the amino acid sequence represented by SEQ ID NO: 20, its partial peptide, or a salt thereof.

(7) A gonadal function improving agent, which comprises a compound or its salt that promotes the activation of a polypeptide comprising the same or substantially the same amino acid sequence as the amino acid sequence represented by SEQ ID NO: 1, or a salt thereof, into a protein comprising the same or substantially the same amino acid sequence as the amino acid sequence represented by SEQ ID NO: 20, its partial peptide, or a salt thereof.

(8) The gonadal function improving agent according to (1) through (7), which is an agent for preventing/treating sterility.

(9) The gonadal function improving agent according to (1) through (7), which is an ovulation inducer or promoter.

(10) The gonadal function improving agent according to (1) through (7), which is a gonadotropic hormone secretion promoter.

(11) The gonadal function improving agent according to (1) through (7), which is a gonadotropic hormone secretion inhibitor.

(12) The gonadal function improving agent according to (1) through (7), which is a sex hormone secretion promoter.

(12a) The gonadal function improving agent according to (12), wherein the sex hormone is an androgen (testosterone, androstenedione, etc.), an estrogen (estradiol, estrone, etc.) or progesterone.

(13) The gonadal function improving agent according to (1) through (7), which is a sex hormone secretion inhibitor.

(13a) The gonadal function improving agent according to (13), wherein the sex hormone is an androgen (testosterone, androstenedione, etc.), an estrogen (estradiol, estrone, etc.) or progesterone.

(14) The gonadal function improving agent according to (1) through (7), which is an agent for preventing/treating a hormone-sensitive cancer.

(15) The gonadal function improving agent according to (1) through (7), which is an agent for preventing/treating endometriosis.

(16) A diagnostic agent for sterility, which comprises a polynucleotide encoding a polypeptide comprising the same or substantially the same amino acid sequence as the amino acid sequence represented by SEQ ID NO: 1, or a salt thereof, or a polynucleotide encoding a protein comprising the same or substantially the same amino acid sequence as the amino acid sequence represented by SEQ ID NO: 20, its partial peptide, or a salt thereof.

(17) A diagnostic agent for sterility, which comprises an antibody to a polypeptide comprising the same or substantially the same amino acid sequence as the amino acid sequence represented by SEQ ID NO: 1, or a salt thereof, or an antibody to a protein comprising the same or substantially the same amino acid sequence as the amino acid sequence represented by SEQ ID NO: 20, its partial peptide, or a salt thereof.

(18) A method of screening for a gonadal function improving agent, which comprises using a polypeptide comprising the same or substantially the same amino acid sequence as the amino acid sequence represented by SEQ ID NO: 1, or a salt thereof, and/or a protein comprising the same or substantially the same amino acid sequence as the amino acid sequence represented by SEQ ID NO: 20, its partial peptide, or a salt thereof.

(19) The screening method according to (18), wherein the gonadal function improving agent is a sex hormone secretion inhibitor or a sex hormone secretion promoter.

(20) The screening method according to (18), wherein the gonadal function improving agent is a gonadotropic hormone secretion inhibitor or a gonadotropic hormone secretion promoter.

(21) A kit for screening for a gonadal function improving agent, which comprises a polypeptide comprising the same or substantially the same amino acid sequence as the amino acid sequence represented by SEQ ID NO: 1, or a salt thereof, and/or a protein comprising the same or substantially the same amino acid sequence as the amino acid sequence represented by SEQ ID NO: 20, its partial peptide, or a salt thereof.

(22) A method of screening for a gonadal function improving agent, which comprises using a polynucleotide encoding a polypeptide comprising the same or substantially the same amino acid sequence as the amino acid sequence represented by SEQ ID NO: 1, or a salt thereof, and/or a polynucleotide encoding a protein comprising the same or substantially the same amino acid sequence as the amino acid sequence represented by SEQ ID NO: 20, its partial peptide, or a salt thereof.

(23) A kit for screening for a gonadal function improving agent, which comprises a polynucleotide encoding a polypeptide comprising the same or substantially the same amino acid sequence as the amino acid sequence represented by SEQ ID NO: 1, or a salt thereof, and/or a polynucleotide encoding a protein comprising the same or substantially the same amino acid sequence as the amino acid sequence represented by SEQ ID NO: 20, its partial peptide, or a salt thereof.

(23a) A gonadal function improving agent, which is obtainable using the screening method according to (18) or (22), or using the screening kit according to (21) or (23).

(23b) The gonadal function improving agent according to (23a), which is an agent for preventing/treating sterility.

(23c) The gonadal function improving agent according to (23a), which is an ovulation inducer or promoter.

(23d) The gonadal function improving agent according to (23a), which is a gonadotropic hormone secretion promoter or inhibitor.

(23e) The gonadal function improving agent according to (23a), which is a sex hormone secretion promoter or inhibitor.

(24) A method of improving gonadal function, which comprises administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(25) A method of improving gonadal function, which comprises (i) promoting the activity of a polypeptide comprising the same or substantially the same amino acid sequence as the amino acid sequence represented by SEQ ID NO: 1, or a salt thereof, (ii) promoting the activity of a protein comprising the same or substantially the same amino acid sequence as the amino acid sequence represented by SEQ ID NO: 20, its partial peptide, or a salt thereof, or (iii) promoting the activation of said polypeptide or a salt thereof into said protein, its partial peptide, or a salt thereof.

(26) Use of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof, to manufacture a gonadal function improving agent.

(27) A method of inhibiting gonadotropic hormone secretion and/or a method of inhibiting sex hormone secretion, which comprises uninterruptedly or continuously administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(27a) A method of inhibiting gonadotropic hormone secretion, which comprises administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof, which dose is sufficient to inhibit gonadotropic hormone secretion, which dose is sufficient to inhibit gonadotropic hormone secretion.

(27b) A method of inhibiting sex hormone secretion, which comprises administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof, which dose is sufficient to inhibit sex hormone secretion, which dose is sufficient to inhibit sex hormone secretion.

(27c) A method of inhibiting gonadotropic hormone secretion, which comprises administering to a mammal an effective dose of an agonist for a protein comprising the same or substantially the same amino acid sequence as the amino acid sequence represented by SEQ ID NO: 20, its partial peptide, or a salt thereof, which dose is sufficient to inhibit gonadotropic hormone secretion, which dose is sufficient to inhibit gonadotropic hormone secretion.

(27d) A method of inhibiting sex hormone secretion, which comprises administering to a mammal an effective dose of an agonist for a protein comprising the same or substantially the same amino acid sequence as the amino acid sequence represented by SEQ ID NO: 20, its partial peptide, or a salt thereof, which dose is sufficient to inhibit sex hormone secretion, which dose is sufficient to inhibit sex hormone secretion.

(27e) A method of inhibiting gonadotropic hormone secretion, which comprises retaining in a mammal at the site or tissue where the pharmaceutical effects are to be exhibited, at a level more than required, (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(27f) A method of inhibiting sex hormone secretion, which comprises retaining in a mammal at the site or tissue where the pharmaceutical effects are to be exhibited, at a level more than required, (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(27g) A method of inhibiting gonadotropic hormone secretion, which comprises retaining in a mammal at the site or tissue where the pharmaceutical effects are to be exhibited, at a level more than required, an agonist for a protein comprising the same or substantially the same amino acid sequence as the amino acid sequence represented by SEQ ID NO: 20, its partial peptide, or a salt thereof.

(27h) A method of inhibiting sex hormone secretion, which comprises retaining in a mammal at the site or tissue where the pharmaceutical effects are to be exhibited, at a level more than required, an agonist for a protein comprising the same or substantially the same amino acid sequence as the amino acid sequence represented by SEQ ID NO: 20, its partial peptide, or a salt thereof.

(28) A method of preventing/treating a hormone-sensitive cancer or endometriosis, which comprises uninterruptedly or continuously administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(28a) A method of preventing/treating a hormone-sensitive cancer or endometriosis, which comprises administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof, which dose is sufficient to give a preventive/therapeutic effect on the hormone-sensitive cancer or endometriosis.

(28b) A method of preventing/treating a hormone-sensitive cancer or endometriosis, which comprises administering to a mammal an effective dose of an agonist for a protein comprising the same or substantially the same amino acid sequence as the amino acid sequence represented by SEQ ID NO: 20, its partial peptide, or a salt thereof, which dose is sufficient to give a preventive/therapeutic effect on the hormone-sensitive cancer or endometriosis.

(28c) A method of preventing/treating a hormone-sensitive cancer or endometriosis, which comprises retaining in a mammal at the site or tissue where the pharmaceutical effects are to be exhibited, at a level more than required, (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(28d) A method of preventing/treating a hormone-sensitive cancer or endometriosis, which comprises retaining in a mammal at the site or tissue where the pharmaceutical effects are to be exhibited, at a level more than required, an agonist for a protein comprising the same or substantially the same amino acid sequence as the amino acid sequence represented by SEQ ID NO: 20, its partial peptide, or a salt thereof.

(29) A method of inhibiting follicular maturation and/or a method of suspending a menstrual cycle, which comprises uninterruptedly or continuously administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(29a) A method of inhibiting follicular maturation and/or a method of suspending a menstrual cycle, which comprises administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof, which dose is sufficient to inhibit the follicular maturation and/or suspend the menstrual cycle.

(29b) A method of inhibiting follicular maturation and/or a method of suspending a menstrual cycle, which comprises administering to a mammal an effective dose of an agonist for a protein comprising the same or substantially the same amino acid sequence as the amino acid sequence represented by SEQ ID NO: 20, its partial peptide, or a salt thereof, which dose is sufficient to inhibit the follicular maturation and/or suspend the menstrual cycle.

(29c) A method of inhibiting follicular maturation and/or a method of suspending a menstrual cycle, which comprises retaining in a mammal at the site or tissue where the pharmaceutical effects are to be exhibited, at a level more than required, (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(29d) A method of inhibiting follicular maturation and/or a method of suspending a menstrual cycle, which comprises retaining in a mammal at the site or tissue where the pharmaceutical effects are to be exhibited, at a level more than required, an agonist for a protein comprising the same or substantially the same amino acid sequence as the amino acid sequence represented by SEQ ID NO: 20, its partial peptide, or a salt thereof.

(30) A method of promoting gonadotropic hormone secretion and/or a method of promoting sex hormone secretion, which comprises applying bolus administration to a mammal in an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(30a) A method of promoting gonadotropic hormone secretion and/or a method of promoting sex hormone secretion, which comprises administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof, which dose is sufficient to promote the gonadotropic hormone secretion and/or promote the sex hormone secretion.

(30b) A method of promoting gonadotropic hormone secretion and/or a method of promoting sex hormone secretion, which comprises retaining in a mammal at the site or tissue where the pharmaceutical effects are to be exhibited, at a level more than required, (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(31) A method of inducing or promoting ovulation, which comprises applying bolus administration to a mammal in an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(31a) A method of inducing or promoting ovulation, which comprises administering to a mammal an effective dose of (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof, which dose is sufficient to induce or promote ovulation.

(31b) A method of inducing or promoting ovulation, which comprises retaining in a mammal at the site or tissue where the pharmaceutical effects are to be exhibited, at a level more than required, (i) a polypeptide comprising the same or substantially the same amino acid sequence as the amino acid sequence represented by SEQ ID NO: 1, or a salt thereof, (ii) a polynucleotide encoding said polypeptide or a salt thereof, (iii) a compound or its salt that promotes the activity of said polypeptide or a salt thereof, (iv) a compound or its salt that promotes the activity of a protein comprising the same or substantially the same amino acid sequence as the amino acid sequence represented by SEQ ID NO: 20, its partial peptide, or a salt thereof, or (v) a compound or its salt that promotes the activation of said polypeptide or a salt thereof into said protein, its partial peptide, or a salt thereof.

(32) A method of inhibiting ovulation, a method of regulating ovarian function, a method of preventing/treating a hormone-sensitive cancer or a method of preventing/treating endometriosis, which comprises administering to a mammal an effective dose of (i) a compound or its salt that inhibits the activity of a polypeptide comprising the same or substantially the same amino acid sequence as the amino acid sequence represented by SEQ ID NO: 1, or a salt thereof, (ii) an antibody to said polypeptide or a salt thereof, (iii) an antisense nucleotide to a polynucleotide encoding said polypeptide or a salt thereof, (iv) a compound or its salt that inhibits the activity of a protein comprising the same or substantially the same amino acid sequence as the amino acid sequence represented by SEQ ID NO: 20, its partial peptide, or a salt thereof, (v) an antibody to the polypeptide or a salt thereof, or (vi) an antisense polynucleotide to a polynucleotide encoding said protein, its partial peptide, or a salt thereof.

(32a) A method of inhibiting ovulation, a method of regulating ovarian function, a method of preventing/treating a hormone-sensitive cancer or a method of preventing/treating endometriosis, which comprises administering to a mammal an effective dose of an antagonist to a protein comprising the same or substantially the same amino acid sequence as the amino acid sequence represented by SEQ ID NO: 20, its partial peptide, or a salt thereof.

BEST MODE FOR CARRYING OUT THE INVENTION

Figure 1:
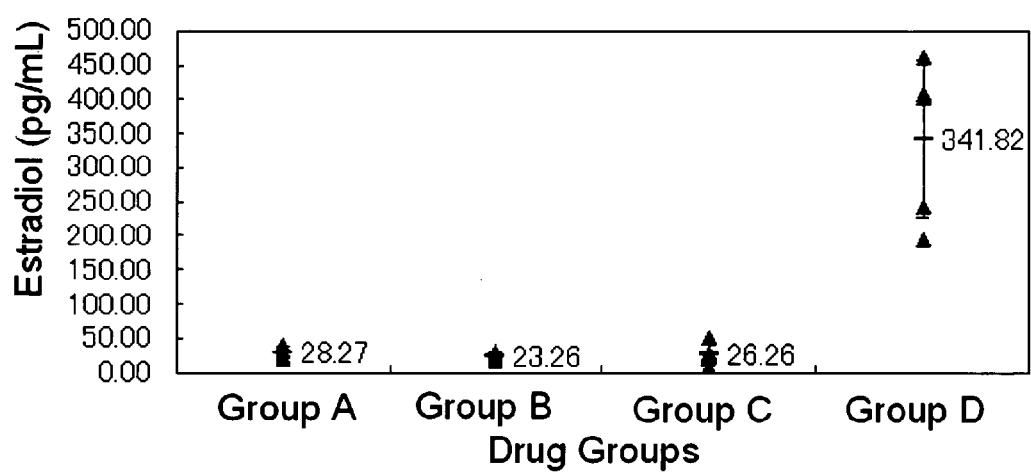
FIG. 1 shows a level of estradiol contained in rat plasma, wherein the ordinate and the abscissa designate the level of estradiol and each group of the drug administration groups, respectively.

The polypeptide comprising the same or substantially the same amino acid sequence as the amino acid sequence represented by SEQ ID NO: 1 (hereinafter sometimes referred to as the polypeptide of the present invention) may be any polypeptide derived from any cells of human and other warm-blooded animals (e.g. guinea pig, rat, mouse, fowl, rabbit, swine, sheep, bovine, monkey, etc.) (for example, retina cell, liver cell, splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., or the corresponding precursor cells, stem cells, cancer cells, etc.), or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; polypeptides derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); the polypeptides may also be synthetic polypeptides.

Substantially the same amino acid sequence as the amino acid sequence represented by SEQ ID NO: 1 includes an amino acid sequence having at least about 70% homology, preferably at least about 80% homology, more preferably at least about 90% homology, much more preferably at least about 95% homology, and most preferably at least about 98% homology, to the amino acid sequence represented by SEQ ID NO: 1.

Specifically, substantially the same amino acid sequence as the amino acid sequence represented by SEQ ID NO: 1 includes:

(i) the amino acid sequence represented by SEQ ID NO: 1, of which 1 to 3 (preferably 1 or 2, preferably 1) amino acids are deleted;

(ii) the amino acid sequence represented by SEQ ID NO: 1, to which 1 to 3 (preferably 1 or 2, preferably 1) amino acids are added;

(iii) the amino acid sequence represented by SEQ ID NO: 1, in which 1 to 3 (preferably 1 or 2, preferably 1) amino acids are inserted;

(iv) the amino acid sequence represented by SEQ ID NO: 1, in which 1 to 3 (preferably 1 or 2, preferably 1) amino acids are substituted with other amino acids; and, (v) a combination of the amino acid sequences (i) through (iv) described above, etc.

Examples of the polypeptide comprising substantially the same amino acid sequence as the amino acid sequence represented by SEQ ID NO: 1 include a polypeptide comprising substantially the same amino acid sequence as the amino acid sequence represented by SEQ ID NO: 1 and having an activity substantially equivalent to that of the amino acid sequence represented by SEQ ID NO: 1, and the like.

The substantially equivalent activity refers to, for example, the activities the polypeptide of the present invention possess (e.g., an activity of binding to receptors or a cell stimulating activity, an action of promoting ovulation, an activity of promoting gonadotropic hormone secretion, an activity of inhibiting gonadotropic hormone secretion, an activity of promoting sex hormone secretion, an activity of inhibiting sex hormone secretion, etc.) and the like. The term substantially equivalent activities are used to mean that these activities are equivalent in nature (for example, biochemically or pharmacologically).

The activity of binding to receptors or the cell stimulating activity can be determined by publicly known methods with some modifications thereof.

The activity of promoting ovulation can be determined by publicly known methods with some modifications thereof, for example, in accordance with the method described in, e.g., European Journal of Endocrinology, 138, 594-600, 1998 or its modifications, the method described in EXAMPLES later stated, etc.

The activity of promoting gonadotropic hormone secretion can be determined by publicly known methods with some modifications thereof, for example, in accordance with the method described in, e.g., Toxicology, 147, 15-22, 2000 or its modifications, the method described in EXAMPLES later stated, etc.

Specific examples of substantially the same amino acid sequence as the amino acid sequence represented by SEQ ID NO: 1 include amino acid sequences represented by SEQ ID NO: 2, SEQ ID NO: 11, SEQ ID NO: 13 or SEQ ID NO: 15, and the like.

Specific examples of the polypeptide comprising the amino acid sequence represented by SEQ ID NO: 1 include amino acid sequences represented by SEQ ID NO: 1 or SEQ ID NO: 9, and the like.

Specific examples of the polypeptide of the present invention include a polypeptide having the amino acid sequence represented by SEQ ID NO: 1 [hereinafter sometimes briefly referred to as human metastin (45-54)], a polypeptide having the amino acid sequence represented by SEQ ID NO: 2 [hereinafter sometimes briefly referred to as mouse metastin (43-52) or rat metastin (43-52)], a polypeptide having the amino acid sequence represented by SEQ ID NO: 3 [hereinafter sometimes briefly referred to as human metastin or human metastin(1-54)], a polypeptide having the amino acid sequence represented by SEQ ID NO: 5 [hereinafter sometimes briefly referred to as mouse metastin], a polypeptide having the amino acid sequence represented by SEQ ID NO: 7 [hereinafter sometimes briefly referred to as rat metastin], a polypeptide having the amino acid sequence represented by SEQ ID NO: 9 [hereinafter sometimes briefly referred to as human metastin (40-54)], a polypeptide having the amino acid sequence represented by SEQ ID NO: 11 [hereinafter sometimes briefly referred to as human metastin (46-54)], a polypeptide having the amino acid sequence represented by SEQ ID NO: 13 [hereinafter sometimes briefly referred to as human metastin (47-54)], a polypeptide having the amino acid sequence represented by SEQ ID NO: 15 [hereinafter sometimes briefly referred to as human metastin (48-54)], and the like.

In various receptors, the receptors to the polypeptide of the present invention are those having the activity of binding to the polypeptide of the present invention, in which the cell-stimulating activity of the receptor-expressed cells (e.g., the activity that promotes arachidonic acid release, acetylcholine release, intracellular $Ca^{2+}$ release, intracellular cAMP production/suppression, intracellular cGMP production, inositol phosphate production, change in cell membrane potential, phosphorylation of intracellular protein, activation of c-fos, pH reduction, GTPγS binding activity, etc.) is observed by the polypeptide of the present invention, and the like. Examples of the receptors include a protein comprising substantially the same amino acid sequence as the amino acid sequence represented by SEQ ID NO: 20, a protein comprising substantially the same amino acid sequence as the amino acid sequence represented by SEQ ID NO: 22, a protein comprising substantially the same amino acid sequence as the amino acid sequence represented by SEQ ID NO: 24, and the like.

The protein comprising the same or substantially the same amino acid sequence as the amino acid sequence represented by SEQ ID NO: 20, the protein comprising the same or substantially the same amino acid sequence as the amino acid sequence represented by SEQ ID NO: 22, and the protein comprising the same or substantially the same amino acid sequence as the amino acid sequence represented by SEQ ID NO: 24 (hereinafter sometimes collectively referred to as the receptor of the present invention) may be any protein derived from any cells of human and other warm-blooded animals (e.g. guinea pig, rat, mouse, fowl, rabbit, swine, sheep, bovine, monkey, etc.) (for example, retina cell, liver cell, splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., or the corresponding precursor cells, stem cells, cancer cells, etc.), or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal code, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; proteins derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.). These proteins may also be synthetic proteins.

The amino acid sequence, which is substantially the same as the amino acid sequence represented by SEQ ID NO: 20, SEQ ID NO: 22 or SEQ ID NO: 24, includes amino acid sequences having at least about 70% homology, preferably at least about 80% homology, and more preferably at least about 90% homology, to the amino acid sequence represented by SEQ ID NO: 20, SEQ ID NO: 22 or SEQ ID NO: 24, etc.

Examples of the protein comprising substantially the same amino acid sequence as the amino acid sequence represented by SEQ ID NO: 20, SEQ ID NO: 22 or SEQ ID NO: 24 include a protein containing substantially the same amino acid sequence as the amino acid sequence represented by SEQ ID NO: 20, SEQ ID NO: 22 or SEQ ID NO: 24 and having an activity substantially equivalent to that of the amino acid sequence represented by SEQ ID NO: 20, SEQ ID NO: 22 or SEQ ID NO: 24, and the like.

The substantially equivalent activities include, for example, an activity of binding to the polypeptide of the present invention, etc. The term substantially equivalent activities are used to mean that these activities are equivalent in nature (for example, biochemically or pharmacologically).

The amino acid sequences, which are substantially the same as the amino acid sequence represented by SEQ ID NO: 20, SEQ ID NO: 22 or SEQ ID NO: 24, include (i) the amino acid sequence represented by SEQ ID NO: 20, SEQ ID NO: 22 or SEQ ID NO: 24, of which 1 to 100 (preferably 1 to 50, preferably 1 to 10, preferably 1 to 5 and preferably 1 to 3) amino acids are deleted; (ii) the amino acid sequence represented by SEQ ID NO: 20, SEQ ID NO: 22 or SEQ ID NO: 24, to which 1 to 100 (preferably 1 to 50, preferably 1 to 10, preferably 1 to 5 and preferably 1 to 3) amino acids are added; (iii) the amino acid sequence represented by SEQ ID NO: 20, SEQ ID NO: 22 or SEQ ID NO: 24, in which 1 to 100 (preferably 1 to 50, preferably 1 to 10, preferably 1 to 5 and preferably 1 to 3) amino acids are inserted; (iv) the amino acid sequence represented by SEQ ID NO: 20, SEQ ID NO: 22 or SEQ ID NO: 24, in which 1 to 100 (preferably 1 to 50, preferably 1 to 10, preferably 1 to 5 and preferably 1 to 3) amino acids are substituted with other amino acids; and, (v) a combination of the amino acid sequences (i) through (iv) described above, etc.

As specific examples of the receptors of the present invention, there are employed, for example, a protein comprising the amino acid sequence represented by SEQ ID NO: 20 (hereinafter sometimes referred to as human OT7T175), a protein comprising the amino acid sequence represented by SEQ ID NO: 22 (hereinafter sometimes referred to as rat OT7T175), a protein comprising the amino acid sequence represented by SEQ ID NO: 24 (hereinafter sometimes referred to as mouse OT7T175), and the like.

Any partial peptide can be used as the partial peptide of the receptor for the polypeptide of the present invention (hereinafter sometimes referred to as the partial peptide of the present invention), as long as it is a partial peptide available for the method of screening for pharmaceutical drugs, etc. later described. Preferably, there may be used partial peptides capable of binding to the polypeptide of the present invention, partial peptides containing the corresponding amino acid sequence in the extracellular region, and the like. In the amino acid sequence which constitutes the receptor of the present invention, desired peptides are those having a sequence of at least 20, preferably at least 50 and more preferably at least 100 amino acids; and the like. They may be peptides having the amino acid sequences described above, (i) of which at least 1 or 2 (preferably approximately 1 to 10, more preferably several (1 to 5)) amino acids are deleted; (ii) to which at least 1 or 2 (preferably approximately 1 to 20, more preferably approximately 1 to 10 and most preferably several (1 to 5)) amino acids are added; (iii) in which at least 1 or 2 (preferably approximately 1 to 10, more preferably several and most preferably approximately 1 to 5) amino acids are substituted by other amino acids.

In the polypeptides, receptors or partial peptides of the present invention, the C-terminus may be in any form of a carboxyl group (—COOH), carboxylate (—COO$^-$), an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; an aralkyl having 7 to 14 carbon atoms such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like, which is used widely as an ester for oral administration, may also be used.

Where the polypeptides, receptors or partial peptides of the present invention contain a carboxyl group (or a carboxylate) at a position other than the C-terminus, it may be amidated or esterified and such an amide or ester is also included within the polypeptide of the present invention. In this case, the ester group may be the C-terminal esters, etc. described above.

The polypeptides, receptors or partial peptides of the present invention further include those wherein the amino group at the N-terminal amino acid residues (e.g., methionine residue) is protected with a protecting group (e.g., a $C_{1-6}$ acyl group, e.g., a $C_{1-6}$ alkanoyl group such as formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (such as a $C_{1-6}$ acyl group, e.g., a $C_{1-6}$ alkanoyl group such as formyl group, acetyl group, etc.), or conjugated proteins such as so-called glycoproteins having sugar chains, and the like.

As salts of the polypeptides, receptors or partial peptides of the present invention, there are used salts with physiologically acceptable acids (e.g., inorganic acids, organic acids) or bases (e.g., alkali metal bases, etc.), or the like, with particular preference in the form of physiologically acceptable acid addition salts. Examples of such salts are salts with inorganic acids (e.g., hydrochloric acid, phosphoric acid, hydrobromic acid, and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptides, receptors or partial peptides of the present invention may be manufactured by a publicly known method used to purify polypeptides from human or other mammalian cells or tissues described above, or may also be manufactured by culturing a transformant containing a DNA encoding the polypeptide, as will be later described. Furthermore, the polypeptides, receptors or partial peptides may also be manufactured by modifications of the protein synthesis, which will be described hereinafter. These polypeptides, receptors or partial peptides may be manufactured by modifications of the methods described in, e.g., WO 00/24890, WO 01/75104, WO 02/072816, etc.

Where the polypeptides, receptors or partial peptides are manufactured from human or mammalian tissues or cells, human or mammalian tissues or cells are homogenized and extracted with an acid or the like, and they are purified and isolated by a combination of chromatography techniques such as reversed phase chromatography, ion exchange chromatography, and the like are carried out on the extract.

To synthesize the polypeptides, receptors or partial peptides of the present invention, or salts thereof, commercially available resins that are used for polypeptide synthesis may normally be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids, in which α-amino groups and functional groups on the side chains are appropriately protected, are condensed on the resin in the order of the sequences of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptides, receptors or partial peptides.

For condensation of the protected amino acids described above, a variety of activation reagents for polypeptide synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide bond-forming reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group for the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the polypeptides, receptors or partial peptides of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group of the peptide chain has been eliminated from the polypeptide and a polypeptide in which only the protecting group of the C-terminal carboxyl group has been eliminated are prepared. The two polypeptides are condensed in a mixture of the solvents described above. The details of the condensation reaction are the same as described above. After the protected polypeptide obtained by the condensation is purified, all the protecting groups are eliminated by the method described above to obtain the desired crude polypeptide. This crude polypeptide is purified by various known purification means. Lyophilization of the major fraction gives the amide of the desired polypeptides or receptors, or partial peptides thereof.

To prepare the esterified polypeptides, receptors or partial peptides of the present invention, for example, the α-carboxyl group of the carboxy terminal amino acid is condensed with a desired alcohol to prepare the amino acid ester, which is followed by procedure similar to the preparation of the amidated protein above to give the desired esterified polypeptides or receptors, or partial peptides thereof.

The polypeptides, receptors or partial peptides of the present invention can be manufactured by publicly known methods for peptide synthesis; or the partial peptides of the receptors may be manufactured by cleaving the receptors with an appropriate peptidase. For the peptide synthesis, for example, either solid phase synthesis or liquid phase synthesis may be used. That is, the partial peptides or amino acids that can construct the polypeptides, receptors or partial peptides of the present invention are condensed with the remaining part. Where the product contains protecting groups, these protecting groups are removed to give the desired peptide. Publicly known methods for condensation and elimination of the protecting groups are described in (a)-(e) below.

(a) M. Bodanszky & M.A. Ondetti: Peptide Synthesis, Interscience Publishers, New York (1966)

(b) Schroeder & Luebke: The Peptide, Academic Press, New York (1965)

(c) Nobuo Izumiya, et al.: *Peptide Gosei-no-Kiso to Jikken* (Basics and experiments of peptide synthesis), published by Maruzen Co. (1975)

(d) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(e) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography, recrystallization, etc. to give the polypeptides, receptors or partial peptides of the present invention. When the polypeptides, receptors or partial peptides of the present invention obtained by the above methods is in a free form, they may be converted into appropriate salts by publicly known methods or modifications thereof; when they are obtained in a salt form, they may be converted into their free form or in the form of different salts by publicly known methods or modifications thereof.

For the DNA encoding the polypeptides, receptors or partial peptides of the present invention, any DNA can be used so long as it contains the base sequence encoding the polypeptides, receptors or partial peptides of the present invention described above. The DNA may be any of genomic DNA, genomic DNA library, cDNA derived from the cells/tissues described above, cDNA library derived from the cells/tissues described above, and synthetic DNA.

The vector to be used for the library may be any of bacteriophage, plasmid, cosmid, phagemid, and the like. In addition, the DNA can be directly amplified by reverse transcriptase polymerase chain reaction (hereinafter abbreviated as RT-PCR) with total RNA or mRNA fraction prepared from the above-described cells or tissues.

The polynucleotide (e.g., DNA) encoding the polypeptide of the present invention may be any DNA, so long as it is, for example, (a) a DNA comprising the base sequence represented by SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 17, SEQ ID NO: 18, or SEQ ID NO: 19, (b) a DNA comprising a base sequence hybridizable under high stringent conditions to the base sequence represented by SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 17, SEQ ID NO: 18, or SEQ ID NO: 19 and encoding a polypeptide which has the activity substantially equivalent to that of the polypeptide of the present invention; etc.

Specific examples of the DNA that is hybridizable under high stringent conditions to the base sequence represented by SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 17, SEQ ID NO: 18, or SEQ ID NO: 19 are DNAs comprising base sequences having at least about 70% homology, preferably at least about 80% homology, more preferably at least about 90% homology and most preferably at least about 95% homology, to the base sequence represented by SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 17, SEQ ID NO: 18, or SEQ ID NO: 19 and the like.

The hybridization can be carried out by publicly known methods or by modifications thereof, for example, according to the method described in Molecular Cloning, 2nd Ed., J. Sambrook et al., Cold Spring Harbor Lab. Press, 1989, etc. A commercially available library may also be used according to the instructions of the attached manufacturer's protocol. The hybridization can be carried out preferably under high stringent conditions.

The high stringent conditions used herein are, for example, those in a sodium concentration at approximately 19 to 40 mM, preferably approximately 19 to 20 mM at a temperature of approximately 50 to 70° C., preferably approximately 60 to 65° C. In particular, hybridization conditions in a sodium concentration at about 19 mM at a temperature of about 65° C. are most preferred.

More specifically, (i) a DNA comprising the base sequence represented by SEQ ID NO: 17, etc. is used as the DNA encoding the polypeptide comprising the amino acid sequence represented by SEQ ID NO: 1;

(ii) a DNA comprising the base sequence represented by SEQ ID NO: 18, a DNA comprising the base sequence represented by SEQ ID NO: 19, etc. are used as the DNA encoding the polypeptide comprising the amino acid sequence represented by SEQ ID NO: 2;

(iii) a DNA comprising the base sequence represented by SEQ ID NO: 4, etc. is used as the DNA encoding the polypeptide comprising the amino acid sequence represented by SEQ ID NO: 3;

(iv) a DNA comprising the base sequence represented by SEQ ID NO: 6, etc. is used as the DNA encoding the polypeptide comprising the amino acid sequence represented by SEQ ID NO: 5;

(v) a DNA comprising the base sequence represented by SEQ ID NO: 8, etc. is used as the DNA encoding the polypeptide comprising the amino acid sequence represented by SEQ ID NO: 7;

(vi) a DNA comprising the base sequence represented by SEQ ID NO: 10, etc. is used as the DNA encoding the polypeptide comprising the amino acid sequence represented by SEQ ID NO: 9;

(vii) a DNA comprising the base sequence represented by SEQ ID NO: 12, etc. is used as the DNA encoding the polypeptide comprising the amino acid sequence represented by SEQ ID NO: 11;

(viii) a DNA comprising the base sequence represented by SEQ ID NO: 14, etc. is used as the DNA encoding the polypeptide comprising the amino acid sequence represented by SEQ ID NO: 13;

(ix) a DNA comprising the base sequence represented by SEQ ID NO: 16, etc. is used as the DNA encoding the polypeptide comprising the amino acid sequence represented by SEQ ID NO: 15; and the like The DNA encoding the receptor of the present invention includes, for example, (i) a DNA comprising the base sequence represented by SEQ ID NO: 21, SEQ ID NO: 23 or SEQ ID NO: 25, or (ii) a DNA having a base sequence hybridizable to the base sequence represented by SEQ ID NO: 21, SEQ ID NO: 23 or SEQ ID NO: 25 under high stringent conditions and (ii) encoding a protein having an activity substantially equivalent to that of the protein comprising the amino acid sequence represented by SEQ ID NO: 21, SEQ ID NO: 23 or SEQ ID NO: 25, and the like. Any of such DNAs may be employed.

Examples of the DNA that is hybridizable to the base sequence represented by SEQ ID NO: 21, SEQ ID NO: 23 or SEQ ID NO: 25 include a DNA containing a base sequence having at least about 70% homology, preferably at least about 80% homology, more preferably at least about 90% homology and most preferably at least about 95% homology, to the base sequence represented by SEQ ID NO: 21, SEQ ID NO: 23 or SEQ ID NO: 25, and the like.

The hybridization can be carried out by publicly known methods or by modifications thereof, for example, according to the method described in Molecular Cloning, 2nd (J. Sambrook et al., Cold Spring Harbor Lab. Press, 1989), etc. A commercially available library may also be used according to the instructions of the attached manufacturer's protocol. The hybridization can be carried out preferably under high stringent conditions.

The high stringent conditions used herein are, for example, those in a sodium concentration at approximately 19 to 40 mM, preferably approximately 19 to 20 mM at a temperature of approximately 50 to 70° C., preferably approximately 60 to 65° C. In particular, hybridization conditions in a sodium concentration at about 19 mM at a temperature of about 65° C. are most preferred.

More specifically, a DNA containing the base sequence represented by SEQ ID NO: 21, or the like is used as the DNA encoding the protein comprising the amino acid sequence represented by SEQ ID NO: 20; a DNA containing the base sequence represented by SEQ ID NO: 23, or the like is used as the DNA encoding the protein comprising the amino acid sequence represented by SEQ ID NO: 22; a DNA containing the base sequence represented by SEQ ID NO: 25, or the like is used as the DNA encoding the protein comprising the amino acid sequence represented by SEQ ID NO: 24.

For the DNA encoding the partial peptide of the receptor of the present invention, any DNA can be used, so far as it contains a base sequence encoding the partial peptide of the receptor of the present invention described above. The DNA may be any of genomic DNA, genomic DNA library, cDNA derived from the cells/tissues described above, cDNA library derived from the cells/tissues described above, and synthetic DNA.

The DNA encoding the partial peptide of the receptor of the present invention includes, for example, a DNA having a partial base sequence of DNA comprising the base sequence represented by SEQ ID NO: 21, SEQ ID NO: 23 or SEQ ID NO: 25, or a DNA comprising a base sequence hybridizable to the base sequence represented by SEQ ID NO: 21, SEQ ID NO: 23 or SEQ ID NO: 25 under high stringent conditions and having a partial base sequence of DNA encoding a protein having an activity substantially equivalent to the protein comprising the amino acid represented by SEQ ID NO: 20, SEQ ID NO: 22 or SEQ ID NO: 24, and the like.

The DNA that is hybridizable to the base sequence represented by SEQ ID NO: 21, SEQ ID NO: 23 or SEQ ID NO: 25 has the same significance as described above.

In the methods for hybridization and high stringent conditions, the same methods and conditions as described above are used.

The DNA encoding the polypeptide, receptor or partial peptide of the present invention may be labeled by public known methods. The labeling agents used for labeling include, for example, radioactive isotopes (e.g., $[^{125}I]$, $[^{131}I]$, $[^{3}H]$, $[^{14}C]$, $[^{32}P]$, $[^{33}P]$, $[^{35}S]$, etc.), fluorescent substances (e.g., cyanine fluorescent dyes (e.g., Cy2, Cy3, Cy5, Cy5.5, Cy7 (manufactured by Amersham Bioscience), etc.), fluorescamine, fluorescein isothiocyanate, and the like.), enzymes (e.g., β-galactosidase, β-glucosidase, alkaline phosphatase, peroxidase, malate dehydrogenase, and the like), luminescent substances (e.g., luminol, luminol derivatives, luciferin, lucigenin, etc.), biotin, lanthanide elements, etc. Preferably used are radioactive isotopes.

For cloning of the DNAs that completely encode the polypeptides, receptors or partial peptides of the present invention (hereinafter these polypeptides, etc. are sometimes collectively referred to as the polypeptide of the present invention in the following description of the cloning and expression of DNAs encoding these polypeptides, etc.), these DNAs may be either amplified by publicly known PCR using synthetic DNA primers containing a part of the base sequence of the polypeptide of the present invention, or the DNA inserted into an appropriate vector can be selected by hybridization with a labeled DNA fragment or synthetic DNA that encodes a part or entire region of the polypeptide of the present invention. The hybridization can be carried out, for example, according to the method described in Molecular Cloning, 2nd (J. Sambrook et al., Cold Spring Harbor Lab. Press, 1989), etc. Where a commercially available library is used, the hybridization can be performed in accordance with the protocol described in the attached instructions.

Conversion of the base sequence of DNA can be effected by publicly known methods such as the ODA-LA PCR method, the Gapped duplex method or the Kunkel method or modification thereof by using a publicly known kit available as Mutan™-Super Express Km, Mutan™-K (both by Takara Shuzo Co., Ltd.), etc.

The cloned DNA encoding the polypeptide can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the polypeptide of the present invention can be manufactured, for example, by (a) excising the desired DNA fragment from the DNA encoding the polypeptide of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, CMV (cytomegalovirus) promoter or SRα promoter is preferably used. Where the host is bacteria of the genus *Escherichia*, preferred examples of the promoter include trp promoter, lac promoter, recA promoter, λP$_L$ promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX)-resistant], ampicillin resistant gene (hereinafter sometimes abbreviated as Amp$^r$), neomycin resistant gene (hereinafter sometimes abbreviated as Neo$^r$, G418-resistant), etc. In particular, when dhfr gene is used as the selection marker using dhfr gene-deficient Chinese hamster cells, recombinants may also be selected on thymidine free media.

If necessary, a signal sequence that matches with a host is added to the N-terminus of the polypeptide of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector bearing the DNA encoding the polypeptide of the present invention thus constructed, transformants can be manufactured.

As the host, there may be employed, e.g., bacteria belonging to the genus *Escherichia*, bacteria belonging to the genus *Bacillus*, yeast, insect cells, insects, animal cells, and the like.

Specific examples of the bacteria belonging to the genus *Escherichia* include *Escherichia coli* K12 DH1 [Proc. Natl. Acad. Sci. USA, 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* M1114 [(Gene, 24, 255 (1983)), 207-21 [Journal of Biochemistry, 95, 87 (1984)], etc.

Examples of yeast include *Saccharomyces cerevisiae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from Estigmena acrea, etc.; and for the virus BmNPV, *Bombyx mori* N cell (BmN cell), etc. is used. Examples of the Sf cell which can be used are Sf9 cell (ATCC CRL1711), Sf21 cell (both cells are described in In Vivo, 13, 213-217 (1977) and the like.

As the insect, for example, a larva of *Bombyx mori* can be used [Nature, 315, 592 (1985)].

Examples of animal cells include monkey cell COS-7, Vero, Chinese hamster cell CHO (hereinafter referred to as CHO cell), dhfr gene deficient Chinese hamster cell CHO (hereinafter simply referred to as CHO (dhfr⁻) cell), mouse L cell, mouse AtT-20, mouse myeloma cell, rat GH3, human FL cell, etc.

Bacteria belonging to the genus *Escherichia* can be transformed, for example, by the method described in Proc. Natl. Acad. Sci. USA, 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. USA, 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the polypeptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary, the culture may be aerated or agitated.

Where the bacteria belonging to the genus *Bacillus* are used as the host, the transformant is cultivated generally at about 30° C. to about 40° C. for about 6 hours to about 24 hours. If necessary, the culture can be aerated or agitated.

Where yeast is used as the host, the transformant is cultivated, for example, in Burkholder's minimal medium [Proc. Natl. Acad. Sci. USA, 77, 4505 (1980)] or in SD medium supplemented with 0.5% Casamino acids [Proc. Natl. Acad. Sci. USA, 81, 5330 (1984)]. Preferably, pH of the medium is adjusted to about 5 to about 8. In general, the transformant is cultivated at about 20° C. to about 35° C. for about 24 hours to about 72 hours. If necessary, the culture can be aerated or agitated.

Where insect cells or insects are used as the host, the transformant is cultivated in, for example, Grace's Insect Medium (Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture can be aerated or agitated.

As described above, the polypeptide of the present invention can be produced in the cell membrane of the transformant, etc.

The polypeptide of the present invention can be separated and purified from the culture described above by the following procedures.

When the polypeptide of the present invention is extracted from the culture or cells, after cultivation the transformant or cell is collected by a publicly known method and suspended in a appropriate buffer. The transformant or cell is then disrupted by publicly known methods such as ultrasonication, a treatment with lysozyme and/or freeze-thaw cycling, followed by centrifugation, filtration, etc. Thus, the crude extract of the polypeptide can be obtained. The buffer used for the procedures may contain a protein modifier such as urea or guanidine hydrochloride, or a surfactant such as Triton X-100™, etc. When the polypeptide is secreted in the culture broth, after completion of the cultivation the supernatant can be separated from the transformant or cell to collect the supernatant by a publicly known method.

The supernatant or polypeptide contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the polypeptide thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide produced by the recombinant can be treated, prior to or after the purification, with an appropriate protein modifying enzyme or proteinase so that the polypeptide can be appropriately modified to partially remove the polypeptide. Examples of these enzymes include trypsin, chymotrypsin, arginyl endopeptidase, protein kinase, glycosidase, and the like.

Antibodies to the polypeptide or receptor of the present invention (hereinafter sometimes briefly referred to as the antibodies of the present invention) may be any of polyclonal antibodies and monoclonal antibodies, as long as they are capable of recognizing the polypeptide or receptor of the present invention.

The antibodies to the polypeptide or receptor of the present invention may be manufactured by publicly known methods for manufacturing antibodies or antisera, using as antigens the polypeptide or receptor of the present invention.

[Preparation of Monoclonal Antibody]

(a) Preparation of Monoclonal Antibody-producing Cells

The polypeptide or receptor of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every 2 to 6 weeks and 2 to 10 times in total. Examples of the applicable warm-blooded animals are monkeys, rabbits, dogs, guinea pigs, mice, rats, sheep, goats and fowl, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion promoter are polyethylene glycol (PEG), Sendai virus, etc.; among them, PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by culturing at 20 to 40° C., preferably at 30 to 37° C. for 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the polypeptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody].

[Preparation of Polyclonal Antibody]

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and a warm-blooded animal is immunized with the complex in a manner similar to the method described above for the manufacture of monoclonal antibodies. The product containing the antibody to the polypeptide of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every 2 to 6 weeks and approximately 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense polynucleotide (preferably DNA) (hereinafter sometimes referred to as the antisense DNA) having a complementary or substantial complementary base sequence to the DNA encoding the polypeptide, receptor or its partial peptide of the present invention (hereinafter sometimes referred to as the DNA of the present invention) can be any antisense DNA so long as it possesses a base sequence complementary or substantially complementary to that of the DNA of the present invention and capable of suppressing expression of the DNA.

The base sequence, which is substantially complementary to the DNA of the present invention, may be, for example, a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). Particularly in the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence, which encodes the N-terminal region of the polypeptide of the present invention, is preferable. These antisense DNAs can be synthesized using a publicly known DNA synthesizer, etc.

The antisense DNA of the present invention may contain changed or modified sugars, bases or linkages. The antisense DNA may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense DNA can be examined using the transformant of the present invention, the gene expression system of the present invention in vivo and in vitro, or the translation system of the peptide or receptor of the present invention in vivo and in vitro.

Hereinafter, applications of (a) the polypeptide of the present invention, (b) the receptor of the present invention (hereinafter, the receptor also includes its partial peptides), (c) the DNA of the present invention, (d) the antibody of the present invention, (e) the antisense DNA, and the like, will be described.

(1) Agents for Preventing/treating Diseases with which the Polypeptide of the Present Invention is Associated The polypeptide of the present invention, which has a cell-stimulating activity of the cells where the receptor of the present invention is expressed and is an endogenous ligand for the receptor of the present invention, possesses the activity of promoting or inhibiting gonadotropic hormones (e.g., FSH, LH, etc.), the activity of promoting or inhibiting the secretion of sex hormones [for example, androgens (e.g., testosterone, androstenedione, etc.), estrogens (e.g., estradiol, estrone, etc.), progesterone, etc.], the gonadal function improving activity, the action of inducing or promoting ovulation, the action on sexual maturation, etc.

Where the polypeptide of the present invention or the DNA of the present invention are found to be abnormal or deficient, or where the receptor of the present invention or the DNA encoding the said receptor are found to be abnormal or deficient, it is highly likely to suffer from, for example, gonadal dysfunction/hypogonadism, sterility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular dysfunction, azoospermia, hypoandrogenemia, etc.] hormone-sensitive cancers (e.g., hormone-sensitive prostate cancer, hormone-sensitive breast cancer, etc.), or to receive an artificial insemination treatment, etc.

Therefore, the polypeptide of the present invention and the DNA of the present invention are useful as gonadal function improving agents, ovulation inducers or promoters, gonadotropic hormone secretion promoters, gonadotropic hormone secretion inhibitors, sex hormone secretion promoters, sex hormone secretion inhibitors, etc., and can be used as agents for preventing/treating, for example, sterility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular dysfunction, azoospermia, hypoandrogenemia, etc.], hormone-sensitive cancers (e.g., hormone-sensitive prostate cancer, hormone-sensitive breast cancer, etc.), endometriosis, etc., ovarian follicular maturation inhibitors, menstrual cycle-suspending agents, or the like. In addition, the polypeptide of the present invention and the DNA of the present invention are useful as gonadotropic hormone secretion suppressors (inhibitors) and (or) sex hormone secretion inhibitors, and can be used as agents for preventing/treating hormone-sensitive cancers or endometriosis, ovarian follicular maturation inhibitors, menstrual cycle-suspending agents, etc., where the polypeptide and the DNA are retained in the site, tissue, etc. where the pharmaceutical effects are to be exhibited, at a level more than required (for example, preferably by continuous administration, sustained administration, etc.). Further by applying, e.g., bolus administration, the polypeptide and the DNA, which are usable as gonadotropic hormone secretion promoters and (or) sex hormone secretion promoters, can be used as, e.g., ovulation inducers or promoters, etc. The continuous administration and sustained administration described above also include a dosing method which involves gradually releasing pharmaceutically active ingredients through bolus administration.

When a patient has a reduced level of, or is deficient of the polypeptide of the present invention in vivo, the polypeptide of the present invention and the DNA of the present invention can provide the role of the polypeptide of the present invention sufficiently or properly for the patient, (a) by administering the DNA of the present invention to the patient to express the polypeptide of the present invention in vivo, (b) by inserting the DNA of the present invention into a cell, expressing the polypeptide of the present invention and then transplanting the cell to the patient, or (c) by administering the polypeptide of the present invention to the patient; etc.

Where the DNA of the present invention is used as the prophylactic/therapeutic agents described above, the DNA per se is administered directly to human or other warm-blooded animal; alternatively, the DNA is inserted into an appropriate vector such as retrovirus vector, adenovirus vector, adenovirus-associated virus vector, etc. The DNA of the present invention may also be administered as naked DNA, or with adjuvants to assist its uptake by gene gun or through a catheter such as a catheter with a hydrogel.

Where the polypeptide of the present invention is used as the aforesaid therapeutic/prophylactic agents, the polypeptide is advantageously used on a purified level of at least 90%, preferably at least 95%, more preferably at least 98% and most preferably at least 99%.

The polypeptide of the present invention can be used orally, for example, in the form of tablets which may be sugar coated if necessary, capsules, elixirs, microcapsules etc., or parenterally in the form of injectable preparations such as a sterile solution and a suspension in water or with other pharmaceutically acceptable liquid. These preparations can be manufactured by mixing the polypeptide of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given. Moreover, the polypeptide of the present invention can also be used as a sustained preparation, which is described in WO 02/85399.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol, polyethylene glycol, etc.), a nonionic surfactant (e.g., polysorbate 80™, HCO-50, etc.), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

The vector in which the DNA of the present invention has been inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded animal (e.g., rat, mouse, guinea pig, rabbit, fowl, sheep, swine, bovine, horse, cat, dog, monkey, etc.).

The dose of the polypeptide of the present invention varies depending on target disease, subject to be administered, route for administration, etc. Where the polypeptide of the present invention is subcutaneously administered for the treatment of, e.g., sterility, the dose is normally about 0.1 mg to about 100 mg, preferably about 1.0 to about 50 mg, and more preferably about 1.0 to about 20 mg per day for adult (as 60 kg body weight). For other animal species, the corresponding dose as converted per 60 kg body weight can be administered.

Furthermore, the polypeptide of the present invention and the DNA of the present invention may be used in combination with other drugs, including alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, Taxol, etc.), cisplatin, carboplatin, etoposide, etc. The polypeptide of the present invention or the DNA of the present invention and the drugs described above may be administered to the patient at the same time or at a different time.

(2) Screening of Drug Candidate Compounds Having the Gonadal Function Improving Action, Sterility-preventing/treating Action, Ovulation Inducing or Promoting Action, Gonadotropic Hormone Secretion Promoting or Inhibiting Action, or Sex Hormone Secretion Promoting or Inhibiting Action The polypeptide of the present invention possesses the action of promoting or inhibiting gonadotropic hormones (e.g., FSH, LH, etc.), the action of promoting or inhibiting sex hormones [for example, androgens (e.g., testosterone, androstenedione, etc.), estrogens (e.g., estradiol, estrone, etc.), progesterone, etc.], the gonadal function improving action, the action of inducing or promoting ovulation, the action on sexual maturation, etc. Therefore, the compound or its salts that promote the activities of the polypeptide of the present invention are useful as, e.g., gonadal function improving agents, ovulation inducers or promoters, gonadotropic hormone secretion promoters, gonadotropic hormone secretion inhibitors, sex hormone secretion promoters, sex hormone secretion inhibitors, etc., and can be used as agents for improving gonadal dysfunction/hypogonadism, agents for preventing/treating, for example, sterility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular dysfunction, azoospermia, hypoandrogenemia, etc.], hormone-sensitive cancers (e.g., hormone-sensitive prostate cancer, hormone-sensitive breast cancer, etc.), endometriosis, etc., ovarian follicular maturation inhibitors, menstrual cycle-suspending agents, or the like. Moreover, when the compound or its salts that promote the activity of the polypeptide of the present invention are retained in the site, tissue, etc., where its pharmaceutical effects are to be exhibited, at a level more than required (for example, preferably by continuous administration, sustained administration, etc.), they are usable as gonadotropic hormone secretion inhibitors and (or) sex hormone secretion inhibitors and can be used as agents for preventing/treating, e.g., hormone-sensitive cancers or endometriosis, etc., ovarian follicular maturation inhibitors, menstrual cycle-suspending agents, or the like. Further by applying, e.g., bolus administration, the compounds, which are useful as gonadotropic hormone secretion promoters and (or) sex hormone secretion promoters, can be used as ovulation inducers or promoters, etc. The continuous administration and sustained administration described above also include a dosing method which involves gradually releasing pharmaceutically active ingredients through bolus administration.

On the other hand, a compound or its salts that inhibit the activities of the polypeptide of the present invention works as ovulation inhibitors, ovarian function regulators, etc. and can be used as, e.g., contraceptives or agents for preventing/treating precocious puberty, hormone-sensitive cancers (e.g., hormone-sensitive prostate cancer, hormone-sensitive breast cancer, etc.), endometriosis, etc.

By using the polypeptide of the present invention, or by constructing the expression system of recombinant polypeptide of the present invention and using the receptor-binding assay system via the expression system, the compound or its salts that alter the binding property of the polypeptide of the present invention to its receptors (the compounds that promote or inhibit the activities of the polypeptide of the present invention) (e.g., peptides, proteins, non-peptide compounds, synthetic compounds, fermentation products, etc.) can be selected. Such compounds include compounds that have the cell-stimulating activity (e.g., the activity that promotes arachidonic acid release, acetylcholine release, intracellular $Ca^{2+}$ release, intracellular cAMP production/suppression, intracellular cGMP production, inositol phosphate production, change in cell membrane potential, phosphorylation of intracellular proteins, activation of c-fos, pH reduction, GTPγS binding activity, etc.) mediated by the receptors of the present invention (i.e., receptor agonists for the polypeptide of the present invention); compounds that do not have the cell-stimulating activity (i.e., receptor antagonists to the polypeptide of the present invention); and the like. The term "alter the binding property to the polypeptide of the present invention" is used to include both cases of inhibiting the binding to the polypeptide of the present invention and promoting the binding to the polypeptide of the present invention.

More specifically, the method of screening for a compound or its salt that promotes or inhibits the activity of the polypeptide of the present invention includes a method of screening for a compound that alters the binding property of the polypeptide of the present invention to its receptors (a compound that promote or inhibit the activity of the polypeptide of the present invention) or a salt thereof, which comprises comparing (i) the case wherein the polypeptide of the present invention is brought in contact with the receptor of the present invention or its partial peptide (hereinafter they are sometimes briefly referred to as the receptor of the present invention) and (ii) the case wherein the polypeptide of the present invention and a test compound are brought in contact with the aforesaid receptor of the present invention.

According to the screening method of the present invention, the method comprises assaying, for example, the binding amount of ligand for the receptor of the present invention, the cell-stimulating activity, or the like, (i) when the polypeptide of the present invention is brought in contact with the receptor of the present invention described above and (ii) when the polypeptide of the present invention and a test compound are brought in contact with the receptor of the present invention described above, and comparing (i) and (ii).

Further specific examples of the screening method of the present invention include:

(a) a method of screening for a compound that alters the binding property of the polypeptide of the present invention to the receptor of the present invention (a compound that promotes or inhibits the activity of the polypeptide of the present invention) or a salt thereof, which comprises assaying the binding amount of a labeled form of the polypeptide of the present invention to the receptor of the present invention, in the case wherein a labeled form of the polypeptide of the present invention is brought in contact with the receptor of the present invention above and in the case wherein a labeled form of the polypeptide of the present invention and a test compound are brought in contact with the receptor of the present invention, and comparing the two cases;

(b) a method of screening for a compound that alters the binding property of the polypeptide of the present invention to the receptor of the present invention (a compound that promotes or inhibits the activity of the polypeptide of the present invention) or a salt thereof, which comprises assaying the binding amount of a labeled form of the polypeptide of the present invention to a cell containing the receptor of the present invention or its cell membrane, in the case wherein a labeled form of the polypeptide of the present invention is brought in contact with the cell containing the receptor of the present invention or its cell membrane and in the case wherein a labeled form of the polypeptide of the present invention and a test compound are brought in contact with the cell containing the receptor of the present invention or its cell membrane, and comparing the two cases;

(c) a method of screening for a compound that alters the binding property of the polypeptide of the present invention to the receptor of the present invention (a compound that promotes or inhibits the activity of the polypeptide of the present invention) or a salt thereof, which comprises assaying the binding amount of a labeled form of the polypeptide of the present invention to the receptor of the present invention, in the case wherein a labeled form of the polypeptide of the present invention is brought in contact with the receptor of the present invention expressed on a cell membrane by culturing a transformant containing a DNA encoding the receptor of the present invention and in the case wherein a labeled form of the polypeptide of the present invention and a test compound are brought in contact with the receptor of the present invention expressed on a cell membrane by culturing a transformant containing a DNA encoding the receptor of the present invention, and comparing the two cases;

(d) a method of screening for a compound that alters the binding property of the polypeptide of the present invention to the receptor of the present invention (a compound that promotes or inhibits the activity of the polypeptide of the present invention) or a salt thereof, which comprises assaying the cell-stimulating activities (e.g., the activities that promote or inhibit arachidonic acid release, acetylcholine release, intracellular $Ca^{2+}$ release, intracellular cAMP production/suppression, intracellular cGMP production, inositol phosphate production, change in cell membrane potential, phosphorylation of intracellular proteins, activation of c-fos, pH reduction, GTPγS binding activity, etc.) mediated by the receptor of the present invention, when a compound that activates the receptor of the present invention (e.g., the polypeptide of the present invention) is brought in contact with a cell containing the receptor of the present invention and when the compound that activates the receptor of the present invention and a test compound are brought in contact with a cell containing the receptor of the present invention, and comparing the activities; and, (e) a method of screening for a compound that alters the binding property of the polypeptide of the present invention to the receptor of the present invention (a compound that promotes or inhibits the activity of the polypeptide of the present invention) or a salt thereof, which comprises assaying the cell-stimulating activities (e.g., the activities that promote or inhibit arachidonic acid release, acetylcholine release, intracellular $Ca^{2+}$ release, intracellular cAMP production/suppression, intracellular cGMP production, inositol phosphate production, change in cell membrane potential, phosphorylation of intracellular proteins, activation of c-fos, pH reduction, GTPγS binding activity, etc.), when a compound that activates the receptor of the present invention (e.g., the polypeptide of the present invention, etc.) mediated by the receptor of the present invention is brought in contact with the receptor of the present invention expressed on a cell membrane by culturing a transformant containing a DNA encoding the receptor of the present invention and when the compound that activates the receptor of the present invention and a test compound are brought in contact with the receptor of the present invention expressed on a cell membrane by culturing a transformant containing a DNA encoding the receptor of the present invention, and comparing the activities; etc.

Preferred examples of the labeled polypeptide of the present invention include a polypeptide comprising the amino acid sequence represented by SEQ ID NO: 1, SEQ ID NO: 2, SEQ ID NO: 3, SEQ ID NO: 5, SEQ ID NO: 7, SEQ ID NO: 9, SEQ ID NO: 11, SEQ ID NO: 13 or SEQ ID NO: 15, each labeled with [$^{125}$I], and the like.

The screening method of the present invention is described below more specifically.

First, the receptor of the present invention, which is used for the screening method of the present invention, may be any protein, so long as it recognizes the polypeptide of the present invention as a ligand, and membrane fractions from human or other warm-blooded animal organs are preferably employed. However, it is very difficult to obtain human-derived organs especially, and the receptor of the present invention, etc. expressed abundantly by use of recombinants are suitable for use in the screening.

In manufacturing the receptor of the present invention, the manufacturing methods described above, etc. are employed.

Where the cell containing the receptor of the present invention or its cell membrane fraction is used in the screening method of the present invention, the method may be carried out in accordance with the procedures later described.

When the cell containing the receptor of the present invention is used, the cell may be fixed with glutaraldehyde, formalin, etc. The fixation may be carried out by a publicly known method.

The cell containing the receptor of the present invention refers to a host cell wherein the receptor of the present invention has been expressed. Examples of such a host cell include *Escherichia coli, Bacillus subtilis*, yeast, insect cells, animal cells, etc. Host cells wherein the receptor of the present invention has been expressed may be prepared in a manner similar to the above-stated method for manufacturing transformants transformed by expression vectors bearing the polypeptide of the present invention.

The membrane fraction refers to a fraction that abundantly contains cell membranes prepared by publicly known methods after disrupting cells. Examples of the cell disruption include cell squashing using a Potter-Elvehjem homogenizer, disruption using a Waring blender or Polytron (manufactured by Kinematica Inc.), disruption by ultrasonication, disruption by cell spraying via a thin nozzle under increasing pressure using a French press, etc., and the like. Cell membranes are fractionated mainly by fractionation using a centrifugal force such as for fractionation centrifugation, density gradient centrifugation, etc. For example, cell disruption fluid is centrifuged at a low rate (500 rpm to 3,000 rpm) for a short period of time (normally about 1 minute to about 10 minutes), the resulting supernatant is then centrifuged at a higher rate (15,000 rpm to 30,000 rpm) normally for 30 minutes to 2 hours. The precipitate thus obtained is used as the membrane fraction. The membrane fraction is rich in the receptor of the present invention expressed and membrane components such as cell-derived phospholipids, membrane proteins, or the like.

The amount of the receptor of the present invention contained in the cells containing the receptor of the present invention or in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the aforesaid (a) through (c) for screening for the compound that alters the binding property of the polypeptide of the present invention to the receptor of the present invention (the compound that promotes or inhibits the activity of the polypeptide of the present invention), an appropriate fraction of the receptor of the present invention and a labeled form of the polypeptide of the present invention, etc. are required. The fraction of the receptor of the present invention is preferably a fraction of a naturally occurring form of the receptor of the present invention or a fraction of a recombinant type of the receptor of the present invention having an equivalent activity. Herein, the term equivalent activity is intended to mean an equivalent ligand binding activity, etc. For example, there may be used polypeptide that are labeled with [$^3$H], [$^{125}$I], [$^{14}$C], [$^{35}$S], etc. Of these, [$^{125}$I]-labeled polypeptide is preferred.

More specifically, the compound that alters the binding property of the polypeptide of the present invention to the receptor of the present invention is screened by the following procedures. First, a receptor preparation is prepared by suspending cells containing the receptor of the present invention or a membrane fraction of the cells in a buffer appropriate for use in the screening method. Any buffer can be used, so long as it does not interfere the polypeptide-receptor binding, including a phosphate buffer or a Tris-HCl buffer, having pH of 4 to 10 (preferably pH of 6 to 8), etc. For the purpose of minimizing non-specific binding, a surfactant such as CHAPS, Tween-80™ (Kao-Atlas Inc.), digitonin, deoxycholate, etc., may optionally be added to the buffer. Further for the purpose of suppressing the degradation of the receptor of the present invention or the polypeptide of the present invention with a protease, a protease inhibitor such as PMSF, leupeptin, E-64 (manufactured by Peptide Institute, Inc.), pepstatin, etc. may also be added. A given amount (5,000 cpm to 500,000 cpm) of a labeled form of the polypeptide of the present invention is added to 0.01 ml to 10 ml of the receptor solution, in which $10^{-10}$ M to $10^{-7}$ M of a test compound is co-present. To determine the amount of non-specific binding (NSB), a reaction tube charged with an unlabeled form of the polypeptide of the present invention in a large excess is also provided. The reaction is carried out at approximately 0° C. to 50° C., preferably 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, the test compound showing the specific binding amount (B minus NSB) of, e.g., 50% or less may be selected as a candidate compound capable of competitive inhibition.

The method (d) or (e) above for screening for the compound that alters the binding property of the polypeptide of the present invention to the receptor of the present invention (the compound that promotes or inhibits the activity of the polypeptide of the present invention) can be performed as follows. For example, the cell stimulating activity (e.g., the activity that promotes or inhibits arachidonic acid release, acetylcholine release, intracellular $Ca^{2+}$ release, intracellular cAMP production/suppression, intracellular cGMP production, inositol phosphate production, change in cell membrane potential, phosphorylation of intracellular proteins, activation of c-fos, pH reduction, GTPγS binding activity, etc.) mediated by the receptor of the present invention may be determined by a publicly known method, or using an assay kit commercially available. Specifically, the cells containing the receptor of the present invention are first cultured on a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., arachidonic acid, etc.) due to a degrading enzyme contained in the cells, an inhibitor against such as a degrading enzyme may be added prior to the assay. The activity such as the cAMP production suppression is detectable as the inhibiting action against the baseline production, which has been increased previously by forskolin or the like.

For screening by assaying the cell stimulating activity, appropriate cells where the receptor of the present invention has been expressed are required. Preferred cells wherein the receptor of the present invention has been expressed are the aforesaid cell line in which the receptor of the present invention has been expressed, etc.

Examples of the test compounds include peptides, proteins, non-peptide compounds, synthetic compounds, fermentation products, cell extracts, plant extracts, animal tissue extracts, etc.

A kit for screening for the compound that alters the binding property of the polypeptide of the present invention to the receptor of the present invention (the compound that promotes or inhibits the activity of the polypeptide of the present invention), or a salt thereof, comprises the receptor of the present invention or its salt, a partial peptide of the receptor of the present invention or its salt, a cell containing the receptor of the present invention or a membrane fraction of the cell containing the receptor of the present invention, and the polypeptide of the present invention.

Examples of the screening kit of the present invention are given below:

1. Reagent for Screening (a) Assay Buffer and Wash Buffer

Hanks' Balanced Salt Solution (manufactured by Gibco Co.) supplemented with 0.05% bovine serum albumin (manufactured by Sigma Corp.).

The solution is sterilized by filtration through a 0.45 μm filter and stored at 4° C. Alternatively, the solution may be prepared at use.

(b) Preparation of the Receptor of the Present Invention

CHO cells on which the receptor of the present invention has been expressed are subcultured in a 12-well plate at the rate of 5×105 cells/well and then cultured at 37° C. under 5% $CO_2$ and 95% air for 2 days.

(c) Labeled Ligand

The polypeptide of the present invention labeled with commercially available [$^3$H], [$^{125}$I], [$^{14}$C], [$^{35}$S], etc. is dissolved in a suitable solvent or buffer. The solution is stored at 4° C. or -20° C., which is diluted to 1 μM with an assay buffer at use.

(d) Standard Ligand Solution

The polypeptide of the present invention is dissolved in PBS supplemented with 0.1% bovine serum albumin (manufactured by Sigma Corp.) in a concentration of 1 mM, and the solution is stored at −20° C.

2. Assay Method (a) Cells are cultured in a 12-well tissue culture plate to express the receptor of the present invention. After washing the cells twice with 1 ml of the assay buffer, 490 μl of the assay buffer is added to each well.

(b) After 5 μl of a test compound solution of $10^{-3}$ to $10^{-10}$ M is added, 5 μl of a labeled form of the peptide of the present invention is added to the system followed by reacting at room temperature for an hour. To determine the amount of the non-specific binding, the polypeptide of the present invention of $10^{-3}$ M is added in an amount of 5 μl, instead of the test compound.

(c) The reaction mixture is removed and washed 3 times with 1 ml each of the wash buffer. The labeled polypeptide of the present invention bound to the cells is dissolved in 0.2N NaOH-1% SDS and mixed with 4 ml of a liquid scintillator A (manufactured by Wako Pure Chemical Industries, Ltd.).

(d) Radioactivity is measured using a liquid scintillation counter (manufactured by Beckmann) and Percent Maximum Binding (PMB) is calculated in accordance with the following equation:

$$PMB=[(B-NSB)/(B_0-NSB)]\times 100$$

wherein:
PMB: percent of the maximum binding
B: value when a sample is added
NSB: non-specific binding
$B_0$: maximum binding The compound or its salt obtainable by the screening method or the screening kit of the present invention is the compound that alters the binding property of the polypeptide of the present invention to the receptor of the present invention (the compound that promotes or inhibits the activity of the polypeptide of the present invention). Specifically, these compounds are compounds or salts thereof that exhibit the cell stimulating activity mediated by the receptor of the present invention (so-called agonists for the receptor of the present invention), or compounds that do not exhibit the cell stimulating activity (so-called antagonists to the receptor of the present invention). Examples of such compounds include peptides, proteins, non-peptide compounds, synthetic compounds and fermentation products. These compounds may be either novel or publicly known compounds.

In order to evaluate whether the compound is the receptor agonist or antagonist of the present invention described above, it is determined by (i) or (ii) below.

(i) According to the screening methods (a) to (c), the binding assay is carried out to obtain the compound that alters the binding property of the polypeptide of the present invention to the receptor of the present invention (especially, the compound that inhibits the binding). Then, it is determined if the compound has the above cell-stimulating activity mediated by the receptor of the present invention. The compound or its salt having the cell-stimulating activity is the receptor agonist of the present invention, whereas the compound or its salt having no such an activity is the receptor antagonist of the present invention.

(ii) (a) A test compound is brought in contact with a cell containing the receptor of the present invention, whereby the aforesaid cell-stimulating activity mediated by the receptor of the present invention is assayed. The compound or its salt having the cell-stimulating activity is the receptor agonist of the present invention.

(b) The cell-stimulating activity mediated by the receptor of the present invention is assayed in the case where a compound that activates the receptor of the present invention (e.g., the polypeptide of the present invention or the receptor agonist of the present invention, etc.) is brought in contact with cells containing the receptor of the present invention and in the case where the compound that activates the receptor of the present invention and a test compound are brought in contact with cells containing the receptor of the present invention, and the cases are compared in terms of the cell-stimulating activity. The compound or its salt that can reduce the cell-stimulating activity induced by the compound that activates the receptor of the present invention is the receptor antagonist of the present invention.

The receptor agonists of the present invention exhibit physiological activities, which are similar to the activities on the receptor of the present invention the polypeptide of the present invention has, and hence are useful as gonadal function improving agents, ovulation inducers or promoters, gonadotropic hormone secretion promoters, gonadotropic hormone secretion inhibitors, sex hormone secretion promoters, sex hormone secretion inhibitors, etc., in the same way as in the polypeptide of the present invention and can be used as safe and non-toxic agents for preventing/treating, for example, sterility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular dysfunction, azoospermia, hypoandrogenemia, etc.], hormone-sensitive cancers (e.g., hormone-sensitive prostate cancer, hormone-sensitive breast cancer, etc.), endometriosis, etc., ovarian follicular maturation inhibitors, menstrual cycle-suspending agents, or the like. The receptor agonists can also be used as ovulation inducers, etc. for an artificial insemination treatment. Besides, in the case that the receptor agonists are retained in the site, tissue, etc., where its pharmaceutical effects are to be exhibited, at a level more than required (for example, preferably by continuous administration, sustained administration, etc.), they can be used as gonadotropic hormone secretion inhibitors and (or) sex hormone secretion inhibitors in agents for preventing/treating, e.g., hormone-sensitive cancers or endometriosis, etc., ovarian follicular maturation inhibitors, menstrual cycle-suspending agents, or the like. Further by applying, e.g., bolus administration, the agonists, which are useful as gonadotropic hormone secretion promoters and (or) sex hormone secretion promoters, can be used as ovulation inducers or promoters, etc. The continuous administration and sustained administration described above also include a dosing method which involves gradually releasing pharmaceutically active ingredients through bolus administration.

The receptor antagonists of the present invention can suppress the physiological activities that the polypeptide of the present invention has on the receptor of the present invention, and hence can be used as, e.g., ovulation inhibitors, ovarian function regulators, etc. for, e.g., contraceptives, agents for preventing/treating precocious puberty, hormone-sensitive cancers (e.g., hormone-sensitive prostate cancer, hormone-sensitive breast cancer, etc.), endometriosis, etc.

The compound or its salt, which is obtainable using the screening method or the screening kit of the present invention, is selected from, e.g., peptides, proteins, non-peptide compounds, synthetic compounds, fermentation products, cell extracts, plant extracts, animal tissue extracts, plasma, etc., and is the compound that promotes or inhibits the activities or functions of the polypeptide of the present invention.

As salts of the compound, there may be used those similar to the salts of the polypeptide of the present invention described above.

When the compound obtained by the screening method or screening kit of the present invention is used as the preventive/therapeutic agents described above, the compound can be prepared into pharmaceutical preparations in a conventional manner. For example, the compound may be prepared in the form of tablets, capsules, elixir, microcapsule, a sterile solution, a suspension, etc., as in the aforesaid drugs containing the polypeptide of the present invention.

Since the thus obtained pharmaceutical preparation is safe and low toxic, the preparation may be administered to human or other warm-blooded animal (e.g., mouse, rat, rabbit, sheep, swine, bovine, horse, fowl, cat, dog, monkey, chimpanzee, etc.).

The dose of the compound or its salt varies depending on its activity, target disease, subject to be administered, route for administration, etc.; for example, where the compound that promotes the activity of the polypeptide of the present invention is subcutaneous administered for the treatment of sterility, the dose is normally about 0.1 to about 100 mg, preferably about 1.0 to about 50 mg, and more preferably about 1.0 to about 20 mg per day for adult (as 60 kg body weight). For other animal species, the corresponding dose as converted per 60 kg body weight can be administered. When the compound that inhibits the activity of the polypeptide of the present invention is administered subcutaneously to an adult (as 60 kg body weight) as a contraceptive, the compound is administered generally in a daily dose of about 0.1 to about 100 mg, preferably about 1.0 to about 50 mg, and more preferably about 1.0 to about 20 mg. For other animal species, the corresponding dose as converted per 60 kg body weight can be administered.

The compound or its salts that promote the activity of the polypeptide of the present invention (e.g., agonists for the polypeptide of the present invention or the receptor of the present invention, etc.) may be used in combination with other drugs, for example, alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, Taxol, etc.), cisplatin, carboplatin, etoposide, etc. The compounds described above or its salts and the drugs described above may be administered to the patient at the same time or at a different time.

(3) Quantification of the Polypeptide of the Present Invention

The antibody of the present invention is capable of specifically recognizing the polypeptide or receptor of the present invention, and can thus be used for quantification of the polypeptide or receptor of the present invention in a sample fluid, in particular, for quantification by sandwich immunoassay, etc.

That is, the present invention provides:

(i) a method for quantification of the polypeptide of the present invention in a sample fluid, which comprises competitively reacting the antibody of the present invention with a sample fluid and a labeled form of the polypeptide of the present invention, and measuring the ratio of the labeled polypeptide of the present invention bound to said antibody; and, (ii) a method for quantification of the polypeptide of the present invention in a sample fluid, which comprises simultaneously or continuously reacting the sample fluid with the antibody of the present invention and a labeled form of another antibody of the present invention immobilized on an insoluble carrier, and measuring the activity of the labeling agent on the immobilized carrier.

In the quantification method (ii) described above, it is preferred that one antibody is capable of recognizing the N-terminal region of the polypeptide of the present invention, while another antibody is capable of recognizing the C-terminal region of the polypeptide of the present invention.

The monoclonal antibody to the polypeptide or receptor of the present invention may be used to quantify the polypeptide or receptor of the present invention. In addition, the polypeptide may also be detected by means of a tissue staining, etc. For these purposes, the antibody molecule per se may be used, or F(ab')2, Fab' or Fab fractions of the antibody molecule may be used as well.

The method of quantifying the polypeptide or receptor of the present invention using the antibody of the present invention is not particularly limited, but any method may be used, so far as it relates to a method, in which the amount of an antibody, antigen or antibody-antigen complex can be detected by a chemical or a physical means, depending on or corresponding to the amount of antigen (e.g., the amount of polypeptide) in a sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

The labeling agents used for the assay method using labeling substances include, for example, radioactive isotopes (e.g., [$^{125}$I], [$^{131}$I], [$^{3}$H], [$^{14}$C], [$^{32}$P], [$^{33}$P], [$^{35}$S], etc.), fluorescent substances [for example, cyanine fluorescent dyes (e.g., Cy2, Cy3, Cy5, Cy5.5, Cy7 (manufactured by Amersham Bioscience), etc.), fluorescamine, fluorescein isothiocyanate, etc.], enzymes (e.g., β-galactosidase, β-glucosidase, alkaline phosphatase, peroxidase, malate dehydrogenase, and the like), luminescent substances (e.g., luminol, luminol derivatives, luciferin, lucigenin, etc.), biotin, lanthanide elements, etc. Furthermore, the biotin-avidin system may be used for binding antibody or antigen to the label.

For immobilization of the antigen or antibody, physical adsorption may be used. Chemical binding methods conventionally used for insolubilization or immobilization of polypeptides, enzymes or the like may also be used. As the carrier, for example, insoluble polysaccharides such as agarose, dextran, cellulose, etc.; synthetic resin such as polystyrene, polyacrylamide, silicon, etc., and glass or the like are used.

In the sandwich method, a sample fluid is reacted with an immobilized form of the monoclonal antibody of the present invention (primary reaction), then reacted with a labeled form of the monoclonal antibody of the present invention (secondary reaction) and the activity of the labeling agent on the insoluble carrier is assayed; thus, the amount of polypeptide of the present invention in a sample fluid can be determined. The primary and secondary reactions may be carried out in a reversed order, simultaneously or sequentially with time intervals. The type of the labeling agent and the method of immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the assay sensitivity, etc.

In the method of assaying the polypeptide of the present invention by the sandwich method according to the present invention, preferred monoclonal antibodies of the present invention used for the primary and the secondary reactions are antibodies, which binding sites to the polypeptide of the present invention are different from each other. Thus, the antibodies used in the primary and secondary reactions are those wherein, when the antibody used in the secondary reaction recognizes the C-terminal region of the polypeptide of the present invention, the antibody recognizing the site other than the C-terminal regions, e.g., recognizing the N-terminal region, is preferably used in the primary reaction.

The monoclonal antibody of the present invention may be used in an assay system other than the sandwich method, such as the competitive method, the immunometric method or the nephrometry.

In the competitive method, an antigen in a sample fluid and a labeled antigen are competitively reacted with an antibody, then an unreacted labeled antigen (F) and a labeled antigen bound to the antibody (B) are separated (i.e., B/F separation) and the labeled amount of either B or F is measured to determine the amount of the antigen in the sample fluid. In the reactions for such a method, there are a liquid phase method in which a soluble antibody is used as the antibody and the B/F separation is effected by polyethylene glycol, while a second antibody to the antibody is used, and a solid phase method in which an immobilized antibody is used as the first antibody or a soluble antibody is used as the first antibody, while an immobilized antibody is used as the second antibody.

In the immunometric method, an antigen in a sample fluid and an immobilized antigen are competitively reacted with a given amount of a labeled antibody followed by separating the solid phase from the liquid phase; or an antigen in a sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the sample fluid.

In the nephrometry, the amount of insoluble sediment, which is produced as a result of the antigen-antibody reaction in a gel or in a solution, is measured. Even when the amount of an antigen in a sample fluid is small and only a small amount of the sediment is obtained, a laser nephrometry utilizing laser scattering can be suitably used.

In applying each of those immunoassays to the assay method of the present invention, any special conditions, operations, etc. are not required. The assay system for the polypeptide of the present invention may be constructed in addition to conditions or operations conventionally used for each of the methods, taking technical consideration by one skilled in the art into account. For the details of such conventional technical means, a variety of reviews, reference books, etc. may be referred to, for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (all published by Academic Press); etc.

As described above, the polypeptide or receptor of the present invention can be quantified with high sensitivity, using the antibody of the present invention.

Furthermore when a reduced level of the polypeptide or receptor of the present invention is detected by quantifying a level of the polypeptide or receptor of the present invention using the antibody of the present invention, it can be diagnosed that one suffers from diseases such as sterility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular dysfunction, azoospermia, hypoandrogenemia, etc.], hormone-sensitive cancers (e.g., hormone-sensitive prostate cancer, hormone-sensitive breast cancer, etc.), endometriosis, etc., or it is highly likely for one to suffer from these disease in the future.

When an increased level of the polypeptide or receptor of the present invention is detected, it can be diagnosed that one suffers from diseases, e.g., precocious puberty, etc., or it is highly likely for one to suffer from such a disease in the future.

The antibody of the present invention can also be employed to detect the polypeptide or receptor of the present invention present in a sample fluid such as body fluids, tissues, etc. The antibody can further be used for the preparation of an antibody column used to purify the polypeptide o or receptor the present invention, detect the polypeptide or receptor of the present invention in each fraction upon purification, analysis of the behavior of the polypeptide or receptor of the present invention in the cells under investigation.

(4) Gene Diagnostic Agent

By using the DNA of the present invention, e.g., as a probe, abnormality (gene abnormality) of the DNA or mRNA encoding the polypeptide of the present invention in human or other warm-blooded animal (e.g., rat, mouse, guinea pig, rabbit, fowl, sheep, swine, bovine, horse, cat, dog, monkey, etc.) can be detected. Thus, the DNA is useful as a gene diagnostic agent for damages, mutation or decreased expression of the DNA or mRNA, or an increased expression or overexpression of the DNA or mRNA; etc.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)), etc.

When a decreased expression of a gene for the polypeptide or receptor of the present invention is detected, e.g., by the Northern hybridization, it can be diagnosed that one is likely to suffer from diseases such as sterility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular dysfunction, azoospermia, hypoandrogenemia, etc.], hormone-sensitive cancers (e.g., hormone-sensitive prostate cancer, hormone-sensitive breast cancer, etc.), endometriosis, etc., or it is highly likely for one to suffer from these disease in the future.

When overexpression of a gene for the polypeptide or receptor of the present invention is detected by the Northern hybridization, it can be diagnosed that one is likely to suffer from diseases such as precocious puberty, etc., or it is highly likely for one to suffer from such a disease in the future.

(5) Pharmaceutical Composition Comprising the Antibody of the Present Invention

The antibody of the present invention (e.g., activated antibody) can be used as, e.g., gonadal function improving agents, ovulation inducers or promoters, gonadotropic hormone secretion promoters, gonadotropic hormone secretion inhibitors, sex hormone secretion promoters, sex hormone secretion inhibitors, etc., and are useful as agents for preventing/treating, for example, sterility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular dysfunction, azoospermia, hypoandrogenemia, etc.], hormone-sensitive cancers (e.g., hormone-sensitive prostate cancer, hormone-sensitive breast cancer, etc.), endometriosis, etc., ovarian follicular maturation inhibitors, menstrual cycle-suspending agents, or the like. Further in the case that the antibody of the present invention (e.g., activated antibody) are retained in the site, tissue, etc., where its pharmaceutical effects are to be exhibited, at a level more than required (for example, preferably by continuous administration, sustained administration, etc.), the antibody can be used as a gonadotropic hormone secretion inhibitor and (or) a sex hormone secretion inhibitor in an agent for preventing/treating, e.g., hormone-sensitive cancers or endometriosis, etc., an ovarian follicular maturation inhibitor, a menstrual cycle-suspending agent, or the like. Further by applying, e.g., bolus administration, the antibody, which is useful as a gonadotropic hormone secretion promoter and (or) a sex hormone secretion promoter, can be used as an ovulation inducer or promoter, etc. The continuous administration and sustained administration described above also include a dosing method which involves gradually releasing pharmaceutically active ingredients through bolus administration.

The neutralizing antibody of the present invention, which is useful as, e.g., an ovulation inhibitor, an ovarian function regulator, etc., can be used as a contraceptive, an agent for preventing/treating, e.g., precocious puberty, hormone-sensitive cancers (e.g., hormone-sensitive prostate cancer, hormone-sensitive breast cancer, etc.), endometriosis, etc.

The agents for diseases described above comprising the antibody of the present invention can be administered orally or parenterally to human or other warm-blooded animal (e.g., rat, rabbit, sheep, swine, bovine, cat, dog, monkey, etc.) either directly as a liquid preparation, or as a pharmaceutical composition in an appropriate preparation form. The dose varies depending on subject to be administered, target disease, conditions, route for administration, etc.; when the antibody of the present invention is used for the treatment/prevention of, e.g., sterility in an adult, the antibody is advantageously administered by intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For other parenteral administration and oral administration, the corresponding dose may be administered. When the conditions are extremely severe, the dose may be increased depending on the conditions.

The antibody of the present invention may be administered directly as it is or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient used for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections, etc. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol or polyethylene glycol), nonionic surfactant [e.g., polysorbate 80, HCO-50 (polyoxyethylene (50 mol) adduct of hydrogenated castor oil)] may be used in combination. For the oily solution, for example, sesame oil, soybean oil and the like are used, and dissolution aids such as benzyl benzoate, benzyl alcohol, etc. may be used in combination. The thus prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody causes any adverse interaction.

Furthermore, the antibody of the present invention may be used in combination with other drugs, including alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, Taxol, etc.), cisplatin, carboplatin, etoposide, etc. The antibody of the present invention and the drugs described above may be administered to the patient at the same time or at a different time.

(6) Pharmaceutical Composition Comprising Antisense DNA

The antisense DNA of the present invention, which is usable as, e.g., an ovulation inhibitor, an ovarian function regulator, etc., can be used as, e.g., contraceptives, agents for preventing/treating, e.g., precocious puberty, hormone-sensitive cancers (e.g., hormone-sensitive prostate cancer, hormone-sensitive breast cancer, etc.), endometriosis, etc.

When the antisense DNA is used, the antisense DNA may be administered directly, or the DNA is inserted into an appropriate vector such as retrovirus vector, adenovirus vector, adenovirus-associated virus vector, etc. and then administered in a conventional manner. The antisense DNA may also be administered as intact DNA, or with adjuvants to assist its uptake by gene gun or through a catheter such as a catheter with a hydrogel.

In addition, the antisense DNA may also be employed as an oligonucleotide probe for diagnosis to examine the presence of the DNA of the present invention in tissues or cells and states of its expression.

(7) DNA Transgenic Animal

The present invention provides a non-human mammal bearing an exogenous DNA encoding the polypeptide or receptor of the present invention (hereinafter merely referred to as the exogenous DNA of the present invention) or its variant DNA (sometimes simply referred to as the exogenous variant DNA of the present invention).

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous DNA of the present invention into a somatic cell, a living organ, a tissue cell, or the like by the DNA transfection methods, and to utilize the transformant for cell culture, tissue culture, etc. In addition, these cells may be fused with the above-described germinal cell by a publicly known cell fusion method to prepare the transgenic animal of the present invention.

Examples of the non-human mammal that can be used include bovine, swine, sheep, goats, rabbits, dogs, cats, guinea pigs, hamsters, mice, rats, and the like. Above all, preferred are rodents, especially mice (e.g., C57BL/6 strain, DBA2 strain, etc. for a pure line and for a cross line, B6C3 µl strain, $BDF_1$ strain $B6D2F_1$ strain, BALB/c strain, ICR strain, etc.) or rats (Wistar, SD, etc.), since they are relatively short in ontogeny and life cycle from a standpoint of preparing model animals for human disease.

"Mammals" in a recombinant vector that can be expressed in the mammals include the aforesaid non-human mammals and human.

The exogenous DNA of the present invention refers to the DNA of the present invention that is once isolated/extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the polypeptide of the present invention, which is abnormal, and exemplified by the DNA that expresses a polypeptide to inhibit the functions of the normal polypeptide of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters, which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the polypeptide of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (a) promoters for the DNA derived from viruses (e.g., simian virus, cytomegalovirus, Moloney leukemia virus, JC virus, breast cancer virus, poliovirus, etc.), and (b) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K1O and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among others them, cytomegalovirus promoters, human polypeptide elongation factor 1α. (EF-1α) promoters, human and chicken β actin promoters etc., which protein can highly express in the whole body are preferred.

It is preferred that the vectors described above have a sequence for terminating the transcription of the desired messenger RNA in the DNA transgenic animal (generally termed a terminator); for example, a sequence of each DNA derived from viruses and various mammals. SV40 terminator of the simian virus, etc. is preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal polypeptide of the present invention can be acquired as a whole or a part of DNA derived from liver, kidney, thyroid cell or fibroblast of human or various mammals (e.g., rabbits, dogs, cats, guinea pigs, hamsters, rats, mice, etc.) or of the genomic DNA from various commercially available genomic DNA libraries, or using as a starting material complementary DNA prepared by a publicly known method from RNA derived from liver, kidney, thyroid cell or fibroblast. Also, an exogenous abnormal DNA can produce a translational region, which is obtained by point mutagenesis variation of the translational region in a normal polypeptide obtained from the cells or tissues described above.

The said translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the exogenous DNA of the present invention is excessively present in all of the germinal cells and somatic cells thereof. The offspring of the animal that inherits the exogenous DNA of the present invention have excessively the exogenous DNA of the present invention in all of the germinal cells and somatic cells thereof.

By acquiring a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the hyperfunction of the polypeptide of the present invention by promoting the function of endogenous normal DNA. Therefore, the animal can be utilized as a pathologic model animal for such a disease. Specifically, using the normal DNA transgenic animal of the present invention, it is possible to elucidate the mechanism of the hyperfunction of the polypeptide of the present invention and the pathological mechanism of the disease associated with the polypeptide of the present invention and to determine how to treat the disease.

In addition, since a mammal transfected the exogenous normal DNA of the present invention exhibits an increasing symptom of the polypeptide of the present invention librated, the animal is usable for screening for therapeutic agents for the disease associated with the polypeptide of the present invention.

On the other hand, non-human mammal having the exogenous abnormal DNA of the present invention can be passaged under normal breeding conditions as the DNA-bearing animal by confirming the stable retaining of the exogenous DNA via crossing. Further, the exogenous DNA to be subjected can be utilized as a starting material by inserting the DNA into the plasmid described above. The DNA construct with promoter can be prepared by conventional DNA engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring passaged the exogenous DNA of the present invention contains the abnormal DNA of the present invention in all of the germinal and somatic cells. A homozygous animal having the introduced DNA on both of homologous chromosomes can be acquired and then by mating these male and female animals, all the offspring can be bled to have the DNA.

Since non-human mammal having the abnormal DNA of the present invention may express the abnormal DNA of the present invention at a high level, the animal may be the function inactivation type inadaptability to the polypeptide of the present invention by inhibiting the function of the endogenous normal DNA and can be utilized as its disease model animal. For example, using the abnormal DNA-transgenic animal of the present invention, it is possible to elucidate the mechanism of inadaptability to the polypeptide of the present invention and to perform to study a method for treatment of this disease.

More specifically, the transgenic animal of the present invention expressing the abnormal DNA of the present invention to a higher level is also expected to serve as an experimental model for elucidation of the mechanism of the functional inhibition (dominant negative effect) of a normal polypeptide by the abnormal polypeptide of the present invention in the function inactive type inadaptability to the polypeptide of the present invention.

A mammal bearing the abnormal exogenous DNA of the present invention is also expected to serve for screening a candidate drug for the treatment of the function inactive type inadaptability to the polypeptide of the present invention, since the polypeptide of the present invention is increased in such an animal in its free form.

Other potential applications of two kinds of the transgenic animals described above include, for example:

(a) use as a cell source for tissue culture;

(b) elucidation of relation to a polypeptide that is specifically expressed or activated by the polypeptide of the present invention, by direct analysis of DNA or RNA in tissue of the DNA transgenic animal of the present invention or by analysis of the polypeptide tissue expressed by the DNA;

(c) research in the function of cells derived from tissues, which are normally difficult to culture, using cells of tissue having the DNA cultured by a standard tissue culture technique;

(d) screening for a drug that enhances the functions of cells using the cells described in (c) above; and, (e) isolation and purification of the variant polypeptide of the present invention and preparation of its antibody.

Furthermore, clinical conditions of a disease associated wit the polypeptide of the present invention, including the function inactive type inadaptability to the polypeptide of the present invention can be determined using the DNA transgenic animal of the present invention. Also, pathological findings on each organ in a disease model associated with the polypeptide of the present invention can be obtained in more detail, leading to the development of a new method for treatment as well as the research and therapy of any secondary diseases associated with the disease.

It is also possible to acquire a liberated DNA-transfected cell by withdrawing each organ from the DNA transgenic animal of the present invention, mincing the organ and digesting with a proteinase such as trypsin, etc., followed by establishing the line of culturing or cultured cells. Furthermore, the DNA transgenic animal of the present invention can serve as identification of cells capable of producing the polypeptide of the present invention, and as studies on association with apoptosis, differentiation or proliferation or on the mechanism of signal transduction in these properties to inspect any abnormality therein. Thus, the DNA transgenic animal can provide an effective research material to elucidate the polypeptide of the present invention and its function and effect.

To develop a therapeutic drug for the treatment of diseases associated with the polypeptide of the present invention, including the function inactive type inadaptability to the polypeptide of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the polypeptide of the present invention, using the DNA transgenic animal of the present invention or a vector capable of expressing the exogenous DNA of the present invention.

(8) Knockout Animal

Both the non-human mammal embryonic stem cell bearing the DNA of the present invention inactivated and the non-human mammal deficient in expressing the DNA of the present invention are used for screening for gonadal function improving agents, preventive/therapeutic agents for sterility, ovulation inducers or promoters, gonadotropic hormone secretion promoters or sex hormone secretion promoters.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the polypeptide of the present invention (hereinafter sometimes referred to as the knockout DNA of the present invention) by substantially inactivating the activity of the polypeptide of the present invention encoded by the DNA (hereinafter merely referred to as ES cell).

As the non-human mammal, the same examples as described above apply.

Strategies for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention the desired non-human mammal has, inserting a reporter gene, etc. including a neomycin resistant gene or a hygromycin resistant gene, or a reporter gene such as lacZ (β-galactosidase gene) or cat (chloramphenicol acetyltransferase gene), etc. into its exon site thereby to disable the functions of exon; or by inserting a DNA sequence which terminates gene transcription (e.g., polyA additional signal, etc.) in the intron between exons thereby to inhibit the synthesis of complete messenger RNA to eventually destroy the gene, transfecting a DNA strand having the thus constructed DNA strand (hereinafter simply referred to as targeting vector) to a chromosome of the subject animal by, e.g., homologous recombination. The thus obtained ES cells are analyzed by the southern hybridization analysis using a DNA sequence on or near the DNA of the present invention as a probe, or by PCR analysis using a DNA sequence on the targeting vector and another DNA sequence near the DNA of the present invention, which is not included in the targeting vector as primers, thereby to select the knockout ES cell of the present invention.

The parent ES cells to inactivate the DNA of the present invention by homologous recombination, etc. may be the strain already established as described above, or may be originally established by the publicly known method by Evans and Kaufman with modifications. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, in addition to the advantages that the ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, the number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is knocked out.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1-10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 other days; it is desirable that cells be observed at passage and cells found to be morphologically abnormal in culture, if any, be abandoned.

Where ES cells are allowed to reach a high density in mono-layers or to form cell aggregates in suspension under appropriate conditions, they will spontaneously differentiate to various cell types, for example, pariental and visceral muscles, cardiac muscle or the like [M. J. Evans and M. H. Kaufman, Nature, 292, 154, 1981; G. R. Martin, Proc. Natl. Acad. Sci. USA, 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention, are useful for studying the polypeptide of the present invention or the receptor of the present invention from an aspect of cell biology.

The non-human mammal deficient in expression of the DNA of the present invention can be identified from a normal animal by measuring the mRNA amount in the subject animal by a publicly known method, and indirectly comparing the levels of expression.

As the non-human mammal, the same examples supra apply.

With respect to the non-human mammal deficient in expression of the DNA of the present invention, the DNA of the present invention can be knocked out by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The cells in which the DNA of the present invention has been knocked out can be identified by the Southern hybridization analysis using a DNA sequence on or near the DNA of the present invention as a probe, or by PCR analysis using as primers a DNA sequence on the targeting vector and another DNA sequence, which is not included in the targeting vector. When non-human mammalian embryonic stem cells are used, a cell line wherein the DNA of the present invention is inactivated by homologous recombination is cloned; the resulting cloned cell line is injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the polypeptide of the present invention. The individuals deficient in homozygous expression of the polypeptide of the present invention or the receptor of the present invention can be obtained from offspring of the intercross between the heterozygotes of the polypeptide of the present invention or the receptor of the present invention.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is knocked out permit passage rearing under ordinary rearing conditions, after the individuals obtained by their crossing have proven to be knocked out.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the polypeptide of the present invention or the receptor of the present invention, such an animal can be a disease model suspected of inactivated biological activities of the polypeptide of the present invention or the receptor of the present invention and thus, offers an effective study to investigate causes for and therapy for these diseases.

(8a) Method of Screening for Compounds Having Therapeutic/preventive Effects on Diseases Caused by Deficiency, Damages, etc. of the DNA of the Present Invention The non-human mammal deficient in expression of the DNA of the present invention can be employed for screening for compounds having therapeutic/preventive effects on diseases caused by deficiency, damages, etc. of the DNA of the present invention.

That is, the present invention provides a method for screening for a compound having therapeutic/preventive effects for diseases caused by deficiency, damages, etc. of the DNA of the present invention, which comprises administering a test compound to the non-human mammal deficient in expression of the DNA of the present invention and observing and measuring a change occurred in the animal.

As the non-human mammal deficient in expression of the DNA of the present invention which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma, etc. These compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/preventive effects of the test compound.

For treating an animal to be tested with a test compound, for example, oral administration, intravenous injection, etc. are applied and the treatment is appropriately selected depending upon conditions of the test animal, properties of the test compound, etc. Furthermore, a dose of test compound to be administered can be appropriately chosen depending on method for administration, nature of test compound, etc.

In the case of screening for, e.g., a gonadal function improving agent, an agent for preventing/treating sterility, an ovulation inducer or promoter, a gonadotropic hormone secretion promoter, a gonadotropic hormone secretion inhibitor, a sex hormone secretion promoter, a sex hormone secretion inhibitor, etc., a non-human mammal deficient in expression of the DNA of the present invention is PMS-treated; the animal is given a test compound 48 hours after the PMS treatment and further 48 hours after, the number of ova, blood hormone level, etc. of the animal are determined with passage of time.

In the screening method above, when a test compound is administered to a test animal and found to increase the number of ova in the test animal to at least about 10%, preferably at least about 30% and more preferably at least about 50%, the test compound can be selected as a compound having a therapeutic/preventive effect on the diseases described above.

The compound obtained by using the screening method above is a compound selected from the test compounds described above and exerts therapeutic/preventive effects on the diseases caused by deficiencies, damages, etc. of the polypeptide of the present invention. Therefore, the compound can be employed as a safe and low toxic drug such as an agent for preventing/treating these diseases. Furthermore, compounds derived from such a compound obtained by the screening described above can be employed as well.

The compound obtained by the screening method above may form a salt thereof. As such a salt, there may be used a salt with a physiologically acceptable acid (e.g., an inorganic acid, an organic acid, etc.) or a base (e.g., an alkali metal salt, etc.), preferably in the form of a physiologically acceptable acid addition salt. Examples of the salt include a salt with an inorganic acid (e.g., hydrochloric acid, phosphoric acid, hydrobromic acid, sulfuric acid, etc.), a salt with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical composition comprising the compound obtained by the above screening method or salts thereof may be manufactured in a manner similar to the method for preparing the pharmaceutical composition comprising the polypeptide of the present invention described hereinabove.

Since the pharmaceutical composition thus obtained is safe and low toxic, it can be administered to human or other mammal (e.g., rat, mouse, guinea pig, rabbit, sheep, swine, bovine, horse, cat, dog, monkey, etc.).

A dose of the compound or its salt to be administered varies depending upon particular disease, subject to be administered, route of administration, etc. and in subcutaneous administration, the compound is administered to an adult patient (as 60 kg body weight) generally in a dose of approximately 0.1 to 100 mg, preferably approximately 1.0 to 50 mg, more preferably approximately 1.0 to 20 mg per day. In parenteral administration, a single dose of the compound may vary depending on the subject to be administered, target disease, etc. but when the compound that promotes the activity of a promoter for the DNA of the present invention is administered to an adult patient (as 60 kg body weight) with sterility in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the corresponding dose as converted per 60 kg body weight can be administered.

(8b) Method of Screening for a Compound that Promotes or Inhibits the Activity of a Promoter for the DNA of the Present Invention The present invention provides a method of screening for a compound or its salt that promotes or inhibits the activity of a promoter for the DNA of the present invention, which comprises administering a test compound to a non-human mammal deficient in expression of the DNA of the present invention and detecting expression of the reporter gene.

In the screening method supra, the non-human mammal deficient in expression of the DNA of the present invention is selected from the aforesaid non-human mammal deficient in expression of the DNA of the present invention, as an animal in which the DNA of the present invention is inactivated by introducing a reporter gene and the reporter gene can be expressed under control of a promoter for the DNA of the present invention.

The same examples of the test compound apply to specific compounds used for the screening.

As the reporter gene, the same specific examples apply to this screening method. Preferably employed are β-galactosidase (lacZ), soluble alkaline phosphatase gene, luciferase gene, and the like.

Since the reporter gene is present under control of a promoter for the DNA of the present invention in the non-human mammal deficient in expression of the DNA of the present invention wherein the DNA of the present invention is replaced by the reporter gene, the activity of the promoter can be detected by tracing the expression of a substance encoded by the reporter gene.

When a part of the DNA region encoding the polypeptide of the present invention is substituted with, e.g., β-galactosidase gene (lacZ) derived from *Escherichia coli*, β-galactosidase is expressed in a tissue where the polypeptide of the present invention should originally be expressed, instead of the polypeptide of the present invention. Thus, the state of expression condition of the polypeptide of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the polypeptide of the present invention, or its tissue slice section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the aforesaid screening method are compounds that are selected from the test compounds described above and the compounds that promote or inhibit the activity of a promoter for the DNA of the present invention.

The compound obtained by the screening method above may form salts. As salts of the compound, there may be used salts with physiologically acceptable acids (e.g., inorganic acids, etc.) or bases (e.g., organic acids, etc.), and especially preferred are physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salts that promote the activity of a promoter for the DNA of the present invention can promote expression of the polypeptide of the present invention thereby to promote the function of the polypeptide and is thus useful as, e.g., gonadal function improving agents, ovulation inducers or promoters, gonadotropic hormone secretion promoters, gonadotropic hormone secretion inhibitors, sex hormone secretion promoters, sex hormone secretion inhibitors, etc. Accordingly, the compound or its salts can be used as agents for preventing/treating, for example, sterility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular dysfunction, azoospermia, hypoandrogenemia, etc.], hormone-sensitive cancers (e.g., hormone-sensitive prostate cancer, hormone-sensitive breast cancer, etc.), endometriosis, etc., ovarian follicular maturation inhibitors, menstrual cycle-suspending agents, or the like. The compound or its salts can also be used as ovulation inducers for artificial insemination, or the like.

The compound or its salts that inhibit the activity of a promoter for the DNA of the present invention can inhibit expression of the polypeptide of the present invention thereby to inhibit the function of the polypeptide and hence, are usable as, e.g., ovulation inhibitors, ovarian function regulators, etc. Thus, the compound or its salts can be used as, e.g., contraceptives or agents for preventing/treating precocious puberty, hormone-sensitive cancers (e.g., hormone-sensitive prostate cancer, hormone-sensitive breast cancer, etc.), endometriosis, etc.

Furthermore, compounds derived from the compounds obtained by the screening described above can also be used as well.

The pharmaceuticals comprising the compound obtained by the screening method or its salt may be manufactured as in the aforesaid pharmaceuticals comprising the polypeptide of the present invention or its salt.

Since the pharmaceutical composition thus obtained is safe and low toxic, it can be administered to human and another mammal (e.g., rat, mouse, guinea pig, rabbit, sheep, swine, bovine, horse, cat, dog, monkey, etc.).

A dose of the compound or its salt to be administered varies depending upon target disease, subject to be administered, route of administration, etc. For example, when a compound that promotes the activity of a promoter for the DNA of the present invention is orally administered, the compound is administered to an adult patient (as 60 kg body weight), generally in a dose of approximately 0.1 to 100 mg, preferably approximately 1.0 to 50 mg and more preferably approximately 1.0 to 20 mg per day. In parenteral administration, a single dose of the compound varies depending upon subject to be administered, target disease, etc. For example, when a compound that promotes the activity of a promoter for the DNA of the present invention is administered to an adult patient (as 60 kg body weight) in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the corresponding dose as converted per 60 kg body weight can be administered.

On the other hand, for example, when a compound that inhibits the activity of a promoter for the DNA of the present invention is orally administered, the compound is administered to an adult patient (as 60 kg body weight) generally in a dose of approximately 0.1 to 100 mg, preferably approximately 1.0 to 50 mg and more preferably approximately 1.0 to 20 mg per day. In parenteral administration, a single dose of the compound varies depending upon subject to be administered, target disease, etc. For example, when a compound that inhibits the activity of a promoter for the DNA of the present invention is administered to an adult patient (as 60 kg body weight) in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the corresponding dose as converted per 60 kg body weight can be administered.

As described above, the non-human mammal deficient in expressing the DNA of the present invention is extremely useful for screening for a compound or its salt that promotes or inhibits the activity of promoter for the DNA of the present invention, and can thus greatly contribute to investigations of causes for various diseases caused by failure to express the DNA of the present invention or to development of preventive/therapeutic agents for these diseases.

Moreover, when a so-called transgenic animal (gene-transfected animal) is prepared by using a DNA containing the promoter region of the polypeptide of the present invention, ligating genes encoding various proteins downstream the same and injecting the genes into animal oocyte, the polypeptide can be specifically synthesized by the animal so that it becomes possible to investigate the activity in vivo. Furthermore, when an appropriate reporter gene is ligated to the promoter region described above to establish a cell line so as to express the gene, such can be used as a survey system of low molecular weight compounds that specifically promotes or suppresses the ability of producing the polypeptide itself of the present invention in vivo.

In the specification and drawings, the codes of bases and amino acids are shown by abbreviations and in this case, they are denoted in accordance with the IUPAC-IUB Commission on Biochemical Nomenclature or by the common codes in the art, examples of which are shown below. For amino acids which may have the optical isomer, L form is presented unless otherwise indicated.

DNA: deoxyribonucleic acid
cDNA: complementary deoxyribonucleic acid
A: adenine
T: thymine
G: guanine
C: cytosine
I: inosine
R: adenine (A) or guanine (G)
Y: thymine (T) or cytosine (C)
M: adenine (A) or cytosine (C)
K: guanine (G) or thymine (T)
S: guanine (G) or cytosine (C)
W: adenine (A) or thymine (T)
B: guanine (G), guanine (G) or thymine (T)
D: adenine (A), guanine (G) or thymine (T)
V: adenine (A), guanine (G) or cytosine (C)
N: adenine (A), guanine (G), cytosine (C) or thymine (T), or unknown or other base
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate ATP: adenosine triphosphate
EDTA: ethylenediaminetetraacetic acid
SDS: sodium dodecyl sulfate
BHA: benzhydrylamine
pMBHA: p-methylbenzhydrylamine
Tos: p-toluenesulfonyl
Bzl: benzyl
Bom: benzyloxymethyl
Boc: t-butyloxycarbonyl
DCM: dichloromethane
HOBt: 1-hydroxybenztriazole
DCC: N,N'-dicyclohexylcarbodiimide
TFA: trifluoroacetic acid
DIEA: diisopropylethylamine
BSA: bovine serum albumin
CHAPS: 3-[(3-cholamidopropyl)dimethylammonio]-1-propanesulphonate.
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
His or H: histidine
Phe or F: phenylalanine
Tyr or Y: tyrosine
Trp or W: tryptophan
Pro or P : proline
Asn or N: asparagine
Gln or Q: glutamine
pGlu: pyroglutamic acid
Tyr (I): 3-iodotyrosine
DMF: N,N-dimethylformamide
Fmoc: N-9-fluorenylmethoxycarbonyl
Trt: trityl
Pbf: 2,2,4,6,7-pentamethyldihydrobenzofuran-5-sulfonyl
Cit: 2-chlorotrityl
But: t-butyl
Met (O): methionine sulfoxide The sequence identification numbers in the sequence listing of the specification indicate the following sequences, respectively.

[SEQ ID NO: 1]
This shows the amino acid sequence of human metastin (45-54).
[SEQ ID NO: 2]
This shows the amino acid sequence of mouse metastin (43-52) and rat metastin (43-52).
[SEQ ID NO: 3]
This shows the amino acid sequence of human metastin.
[SEQ ID NO: 4]
This shows the base sequence of DNA encoding human metastin.
[SEQ ID NO: 5]
This shows the amino acid sequence of mouse metastin.
[SEQ ID NO: 6]
This shows the base sequence of cDNA encoding mouse metastin.
[SEQ ID NO: 7]
This shows the amino acid sequence of rat metastin.
[SEQ ID NO: 8]
This shows the base sequence of cDNA encoding rat metastin.
[SEQ ID NO: 9]
This shows the amino acid sequence of human metastin (40-54).
[SEQ ID NO: 10]
This shows the base sequence of DNA encoding human metastin (40-54).
[SEQ ID NO: 11]
This shows the amino acid sequence of human metastin (46-54).
[SEQ ID NO: 12]
This shows the base sequence of DNA encoding human metastin (46-54).
[SEQ ID NO: 13]
This shows the amino acid sequence of human metastin (47-54).
[SEQ ID NO: 14]
This shows the base sequence of DNA encoding human metastin (47-54).
[SEQ ID NO: 15]
This shows the amino acid sequence of human metastin (48-54).
[SEQ ID NO: 16]
This shows the base sequence of DNA encoding human metastin (48-54).
[SEQ ID NO: 17]
This shows the base sequence of DNA encoding human metastin (45-54).
[SEQ ID NO: 18]
This shows the base sequence of DNA encoding mouse metastin (43-52).
[SEQ ID NO: 19]
This shows the base sequence of DNA encoding rat metastin (43-52).
[SEQ ID NO: 20]
This shows the amino acid sequence of human OT7T175.
[SEQ ID NO:21]
This shows the base sequence of cDNA encoding human OT7T175.
[SEQ ID NO: 22]
This shows the amino acid sequence of rat OT7T175.
[SEQ ID NO: 23]
This shows the base sequence of cDNA encoding rat OT7T175.
[SEQ ID NO: 24]
This shows the amino acid sequence of mouse OT7T1 75.
[SEQ ID NO: 25]
This shows the base sequence of cDNA encoding mouse OT7T175.

Hereinafter, the present invention is described in more detail with reference to EXAMPLES AND PREPARATION EXAMPLE, but is not deemed to limit the scope of the present invention thereto.

EXAMPLE 1

Induction of Ovulation in Immature Rats by Human Metastin

Equine chorionic gonadotropin (eCG, Serotropin, Dainippon Pharmaceutical Co., Ltd.) was dissolved in physiological saline (Otsuka Pharmaceutical Co., Ltd.) in 100 IU/mL. From 9:30 to 10:00 AM, female Wistar rats of 23 days old after birth (Nippon Charles River) received 10 IU of eCG per animal subcutaneously in the back through a 1 mL tuberculin syringe with a 26 gauge needle (both by Terumo). The rats were assigned to the following groups 47 to 48 hours after the administration of eCG, to each of which groups a drug was given.

Group A (five rats): Human chorionic gonadotropin (hCG, Gonadotropin, Dainippon Pharmaceutical Co., Ltd.) was dissolved in physiological saline in 100 IU/mL and 20 IU/animal was subcutaneously administered in the back.

Group B (five rats): Human metastin was dissolved in physiological saline in 100 nmol/mL and 20 nmol/animal was subcutaneously administered in the back.

Group C (five rats): Human metastin was dissolved in physiological saline in 33.3 nmol/mL and 6.67 nmol/animal was subcutaneously administered in the back.

Group D (six rats): Physiological saline, 200 µL, was subcutaneously administered in the back.

After administration of the drug described above, the animals were sacrificed after additional 24 to 25 hours by decapitation to collect blood, bilateral uterine tubes and uterus. Before blood collection, 90 µL of 10 KIU/mL aprotinin solution (Trasylol, Bayer) supplemented with 3 mg /mL EDTA was previously filled in a centrifuging tube for collection to prevent blood clotting. After the blood collection, the blood was thoroughly stirred and centrifuged at 2,000 G for 25 minutes. The supernatant was recovered and used as a plasma sample.

The number of ova was counted as follows.

Where retained ova in the ampulla of uterine tube were confirmed by stereomicroscopic observation of the uterine tube, the ampulla was punctured with a 27-gauge syringe needle (Terumo) to retrieve the ova. After granulosa cells surrounding the ova were removed by trypsin treatment, the number of ova was counted. Where the retained ova in the ampulla of uterine tube were not confirmed by stereomicroscopic observation of the uterine tube, a 27-gauge syringe needle with the polished tip was inserted into the tubal ostium and more than 400 µL of saline was flushed into the uterine tube and uterus for rinsing. Then, the presence or absence of ova in the effluent was observed.

The number of ova obtained is shown in Table 1.

TABLE 1

|   | Group A | Group B | Group C | Group D |
|---|---------|---------|---------|---------|
| 1 | 36 | 29 | 29 | 0 |
| 2 | 35 | 56 | 39 | 0 |
| 3 | 40 | 17 | 32 | 0 |
| 4 | 42 | 25 | 22 | 0 |
| 5 | 35 | 32 | 16 | 0 |
| Average number of ova | 37.6 | 31.8 | 27.6 | 0.00 |
| Standard deviation | 3.21 | 14.65 | 8.91 | 0.00 |

In the table, numerals 1 to 5 indicate rat identification number.

In Group A, which is a multipurpose superovulation treatment group, ovulation of 37.6 ova in average per rat was confirmed. In Groups B and C receiving the metastin, ovulation of 31.8 and 27.6 ova in average were confirmed, respectively. Turning to Group D receiving saline, the number of ova was 0.6 in average, indicating that voluntary ovulation was little observed without ovulation stimulation.

The level of estradiol contained in plasma collected from the rats shown in Table 1 was determined by radioimmunoassay (DPC-Estradiol Kit; Diagnostic Products Corporation). The results are shown in FIG. 1.

The results reveal that among Groups A, B and C, there is no difference in the level of estradiol contained in plasma, showing that the level of estradiol was extremely high only in Group D receiving saline.

Figure 2:
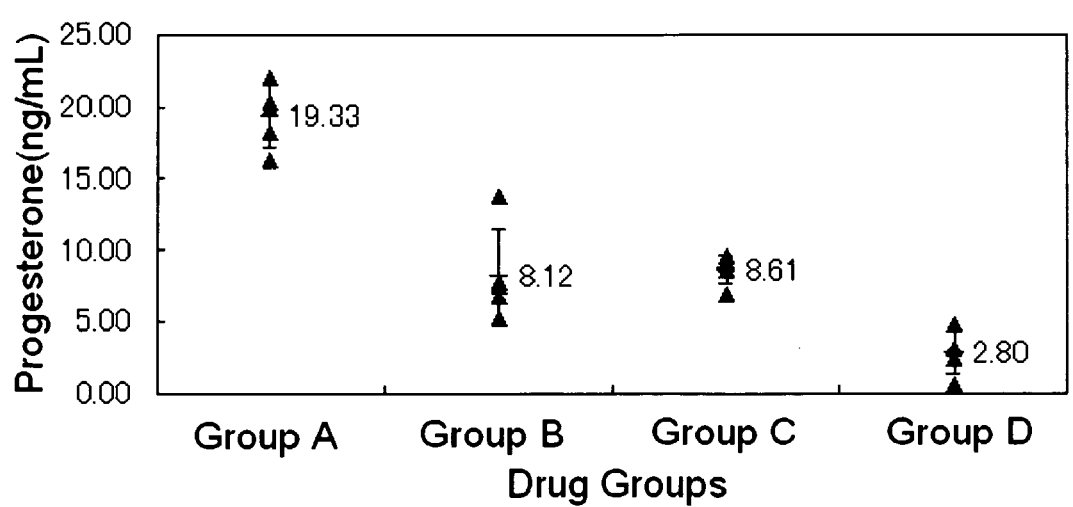
FIG. 2 shows a level of progesterone contained in rat plasma, wherein the ordinate and the abscissa designate the level of progesterone and each group of the drug administration groups, respectively.

The level of progesterone contained in plasma was determined by radioimmunoassay (DPC.Progesterone; Diagnostic Products Corporation). The results are shown in FIG. 2.

The results reveal that the level of progesterone was the highest in Group A and in Groups B and C, the plasma level was approximately half that of Group A. The results also reveal that the progesterone level was extremely low in Group D.

In general, the major steroid hormone produced in rat, mouse and human ovaries is estrogen in the mature phase of ovarian follicle, whereas the hormone is progesterone after ovulation was induced. In fact, it is understood also from the results shown in FIGS. 1 and 2 that Group D receiving saline maintained the state where estrogen was highly produced, because of no induction of ovulation; whereas in Group A receiving hCG; estrogen production decreased but progesterone production increased. In Groups B and C, which are groups receiving the metastin, the plasma estrogen level was very low but the progesterone level increased, indicating that the metastin induced ovulation in the rat ovary via its normal ovulatory process. Since the progesterone level in Groups B and C was lower than in Group A, it is considered that the metastin would have a milder ovarian stimulation, when compared to hCG.

EXAMPLE 2

Gonadotropin-releasing Effect of Human Metastin in Immature Rats

Human metastin dissolved in saline in a concentration of 33.3 nmol/mL was subcutaneously injected into the dorsal area of female Wistar rats of 25 days old after birth (Charles River Japan, Inc.) in a dose of 200 µL/animal, i.e., 6.67 nmol as human metastin, between 9:00 and 10:00 AM. Prior to the metastin injection and 1, 2 and 4 hours after the injection, the animal was sacrificed by decapitation to collect blood. In blood collection, 90 µL of 10 KIU/mL aprotinin solution (Trasylol, Bayer) containing 3 mg/mL EDTA had been previously filled in a centrifuging tube for blood collection to prevent blood clotting. After the blood collection, the blood was thoroughly stirred and centrifuged at 2,000 G for 25 minutes. The supernatant was recovered and used as a plasma sample. The levels of FSH (follicle-stimulating hormone), LH (luteinizing hormone) and progesterone contained in plasma were determined by radioimmunoassay (Rat Follicle Stimulating Hormone (rFSH) [$^{125}$I] Biotrack Assay System with Magnetic Separation, Rat Luteinizing Hormone (rLH) [$^{125}$I] Biotrack Assay System with Magnetic Separation, all by Amersham Biosciences, and DPC.Progesterone by Diagnostic Products Corporation).

Figure 3:
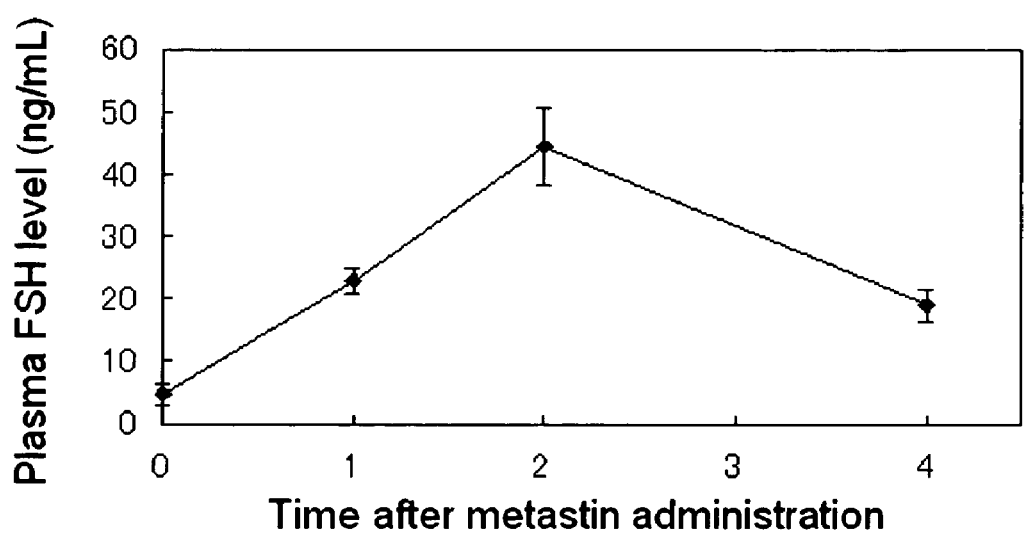
FIG. 3 shows changes of FSH level in immature rat plasma after administration of metastin.

The results obtained by monitoring changes in the FSH level in plasma from the immature rats by the metastin injection are shown in FIG. 3. One hour after the metastin injection, the plasma FSH level began to significantly increase and reached the maximum 2 hours after. While a decrease in the plasma FSH level was noted 4 hours after, the FSH level was still maintained higher than the level prior to the injection.

Figure 4:
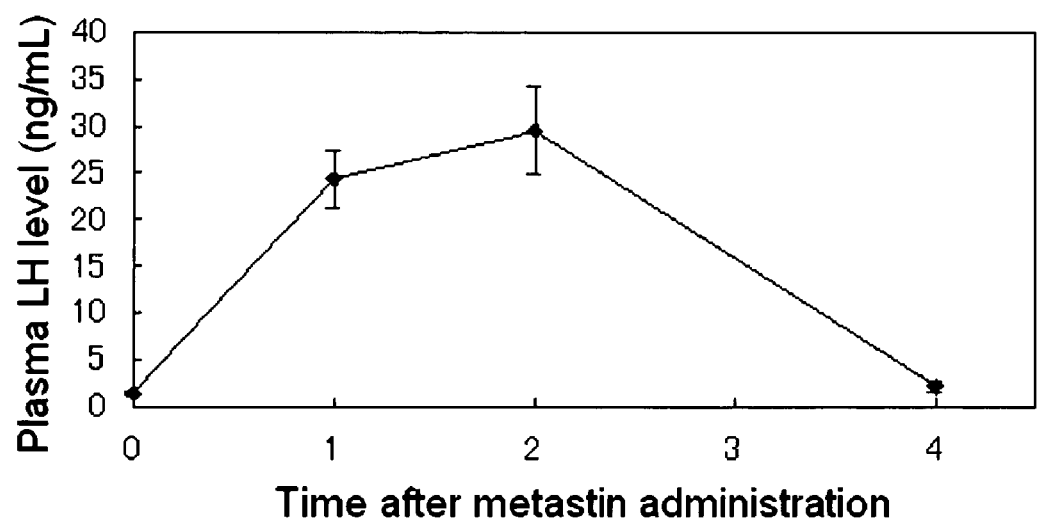
FIG. 4 shows changes of LH level in immature rat plasma after administration of metastin.

The results obtained by monitoring changes in the LH level in plasma from the immature rats by the metastin injection are shown in FIG. 4. Similarly to the case of FSH, the plasma LH level began to significantly increase 1 hour after and reached the maximum 2 hours after. While a decrease in the plasma LH level was noted 4 hours after, the LH level was still maintained higher than the level prior to the injection.

Figure 5:
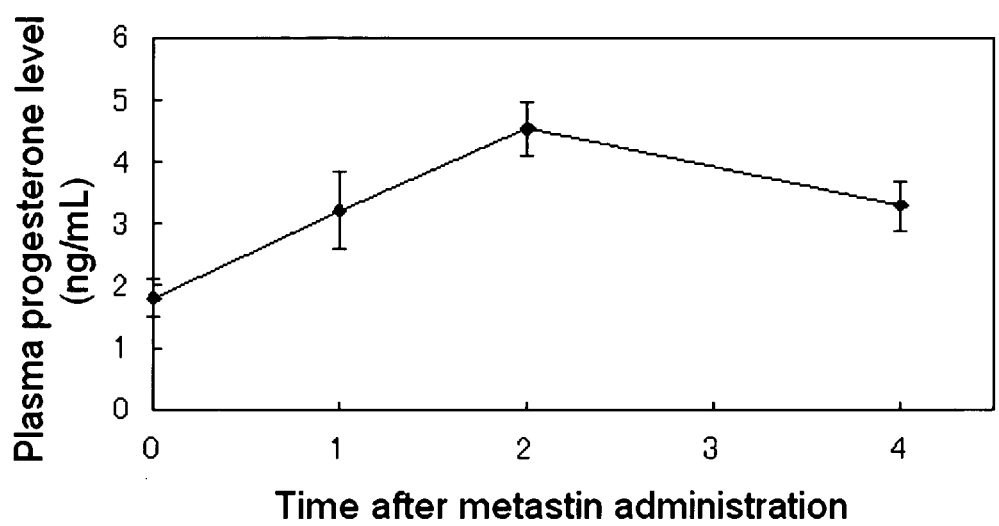
FIG. 5 shows changes of progesterone level in immature rat plasma after administration of metastin.

The results obtained by monitoring changes in the progesterone level in plasma from the immature rats by the metastin injection are shown in FIG. 5. Reflecting the increased plasma LH level, the progesterone level in plasma began to gently increase 1 hour after the metastin injection and showed a significantly higher level 2 hours after, than the level prior to the injection.

The results shown in FIGS. 3 and 4 reveal that peripheral administration of the metastin induces release of gonadotropins such as FSH, LH, etc. The induction of ovulation by the metastin demonstrated in EXAMPLE 1 is considered to be mediated by this gonadotropin release, particularly LH release.

The effect of inducing ovulation demonstrated in EXAMPLE 1 is an effect in rats receiving eCG but the effect in this EXAMPLE shows the results obtained using intact rats. No eCG pretreatment is required for the effect of releasing gonadotropins by the metastin.

The results shown in FIG. 5 mean that the release of gonadotropins by the metastin injection imparts physiological stimulation also to the ovary, resulting in increased production of progesterone.

EXAMPLE 3

Gonadotropin-releasing Effect in Mature Male Rats by Human Metastin

Human metastin dissolved in saline in a concentration of 175 nmol/mL was subcutaneously injected into the dorsal area of male Wistar rats of 11 weeks old after birth (Charles River Japan, Inc.) in a dose of 200 μL/animal, i.e., 35 nmol as human metastin, between 10:30 and 11:30 AM. Prior to the metastin injection and 1, 2 and 4 hours after the injection, the animal was sacrificed by decapitation to collect blood. In blood collection, 300 μL of 10 KIU/mL aprotinin solution (Trasylol, Bayer) containing 3 mg/mL EDTA had been previously filled in a centrifuging tube for blood collection to prevent blood clotting. After blood collection, the blood was thoroughly stirred and centrifuged at 2,000 G for 25 minutes. The supernatant was recovered and used as a plasma sample. The levels of FSH (follicle-stimulating hormone), LH (luteinizing hormone) and testosterone contained in plasma were determined by radioimmunoassay (Rat Follicle Stimulating Hormone (rFSH) [$^{125}$I] Biotrack Assay System with Magnetic Separation, Rat Luteinizing Hormone (rLH) [$^{125}$I] Biotrack Assay System with Magnetic Separation, all by Amersham Biosciences, and DPC.Total Testosterone by Diagnostic Products Corporation).

Figure 6:
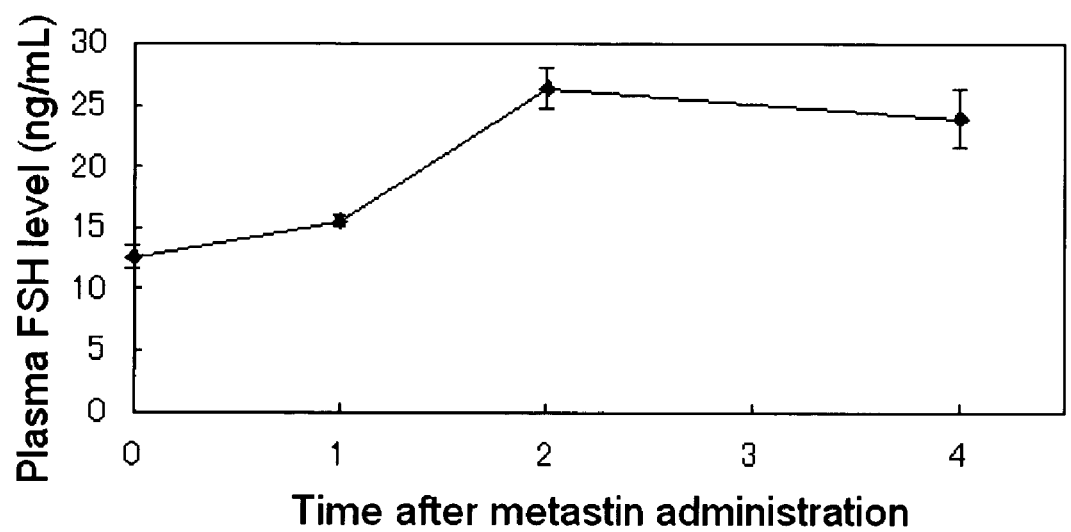
FIG. 6 shows changes of FSH level in rat plasma after administration of metastin.

The results obtained by monitoring changes in the plasma FSH level in rats by the metastin injection are shown in FIG. 6. One hour after the metastin injection, the plasma FSH level began to significantly increase and reached the maximum after 2 hours, and even after 4 hours, still maintained a higher state.

Figure 7:
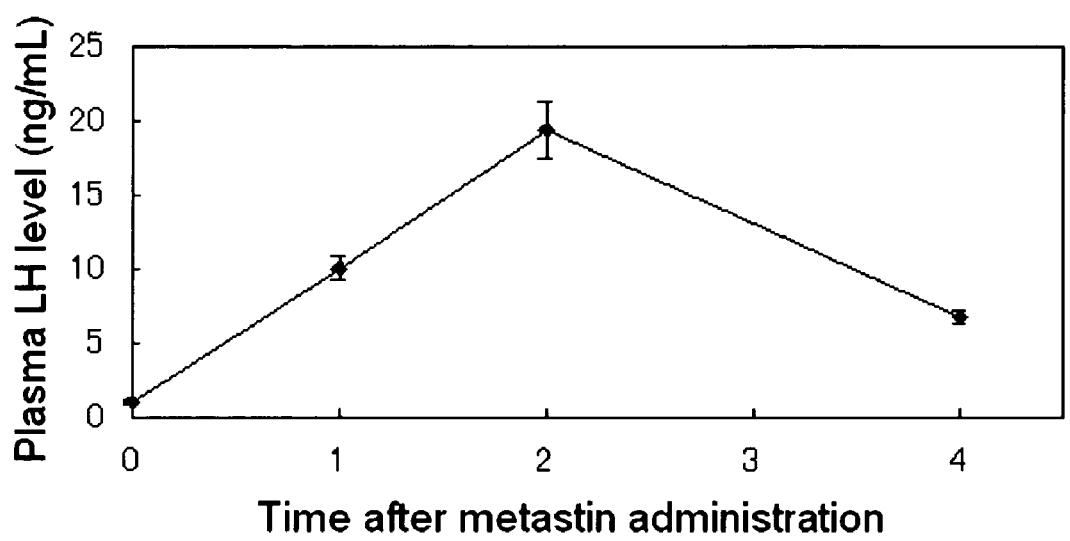
FIG. 7 shows changes of LH level in rat plasma after administration of metastin.

The results obtained by monitoring changes in the plasma LH level in rats by the metastin injection are shown in FIG. 7. Similarly to the case of FSH, the plasma LH level began to significantly increase 1 hour after and reached the maximum 2 hours after. While a decrease in the plasma LH level was noted 4 hours after, the LH level was still maintained higher than the level prior to the injection.

Figure 8:
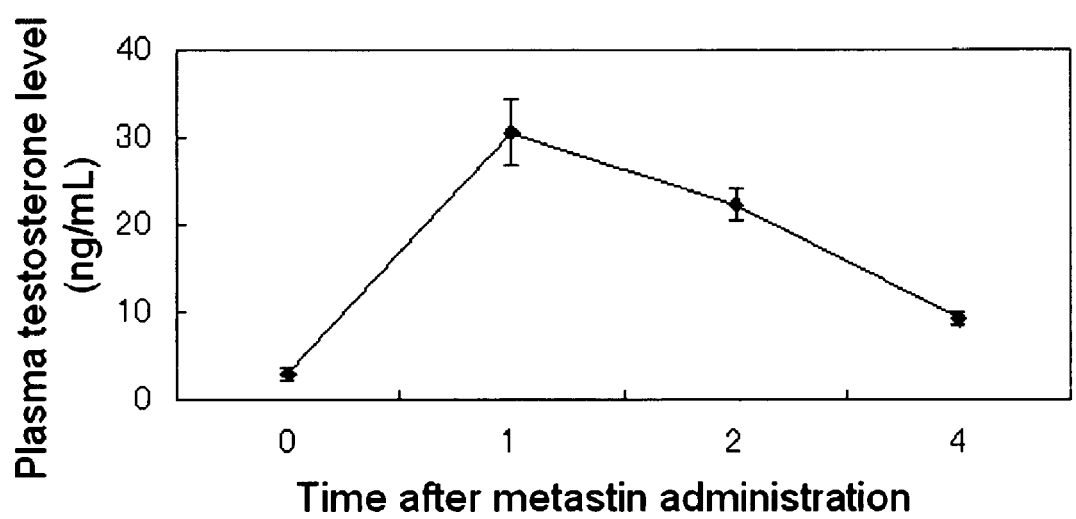
FIG. 8 shows changes of testosterone level in rat plasma after administration of metastin.

The results obtained by monitoring changes in the plasma testosterone level in rats by the metastin injection are shown in FIG. 8. The plasma testosterone level showed a rapid increase in 1 hour after the metastin injection. While a decrease in the testosterone level was noted 2 and 4 hours after, the testosterone level was still maintained at any point of time, which was higher than the level prior to the injection.

The results of FIGS. 6 and 7 reveal that peripheral administration of the metastin induces release of gonadotropins such as FSH, LH, etc. in male rats. In view of the results of EXAMPLE 1, the metastin is considered to be an extremely important factor in both female and male rats, for stimulating the release of gonadotropins.

The results shown in FIG. 8 mean that the release of gonadotropins by the metastin injection imparts physiological stimulation also to the testis, resulting in increased production of testosterone.

From these results it is considered that administration of the metastin would stimulate the testis mediated by the release of gonadotropins. This suggests that the metastin possibly affects the male reproductive function including seminal maturation, hormone secretion, etc.

EXAMPLE 4

Down-regulation Action of Testosterone on Mature Male Rats using Human Metastin Peptide Male Copenhagen rats of 8 weeks old after birth (Charles River Laboratories, US) were anesthetized by giving an intraperitoneal injection of sodium pentobarbital (Nembutal, Dainippon Pharmaceutical Co., Ltd.) in a dose of 50 mg/kg body weight. Then, two ALZET osmotic pumps (Model 2001, volume: 200 μL, rate: 1.0 μL/hr) filled with a 3 mM human metastin solution in distilled water (metastin group) or with distilled water (distilled water group) were implanted subcutaneously in rats at the back (5 rats in each group), whereby human metastin was continuously administered at a rate of 6.0 nmol/hr in the metastin group. For the intraperitoneal administration of sodium pentobarbital, a 1 mL tuberculin syringe and a 26-gauge needle (both by Terumo Co., Ltd.) were used. Following weighing the body weight 7 days after the implantation of the pumps, the animal was sacrificed by decapitation to collect blood. At the same time, the weight of testis was weighed. The level of human metastin in plasma was assayed by enzyme immunoassay (EIA) (J. Clin. Endocrinol. Metab. 88(2): 914-919 (2003)). The levels of FSH (follicle-stimulating hormone), LH (luteinizing hormone) and testosterone contained in plasma were determined by radioimmunoassay (Rat Follicle Stimulating Hormone (rFSH) [$^{125}$I] Biotrack Assay System with Magnetic Separation, Rat Luteinizing Hormone (rLH) [$^{125}$I] Biotrack Assay System with Magnetic Separation, all by Amersham Biosciences, and DPC.Total Testosterone by Diagnostic Products Corporation).

The assay results are shown in FIGS. 9 through 12.

A mean level of human metastin after the sustained administration of human metastin was approximately 3.2 pmol/mL.

Figure 9:
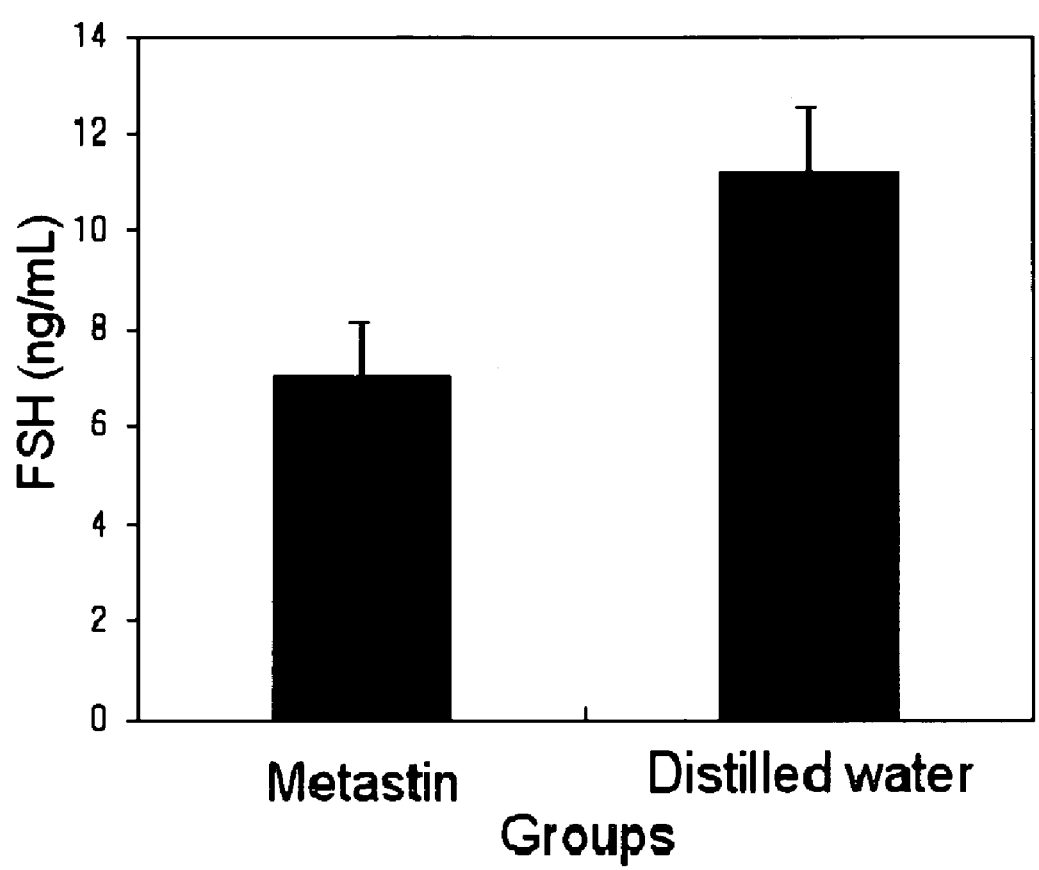
FIG. 9 shows FSH level in rat plasma after sustained administration of human metastin.
Figure 10:
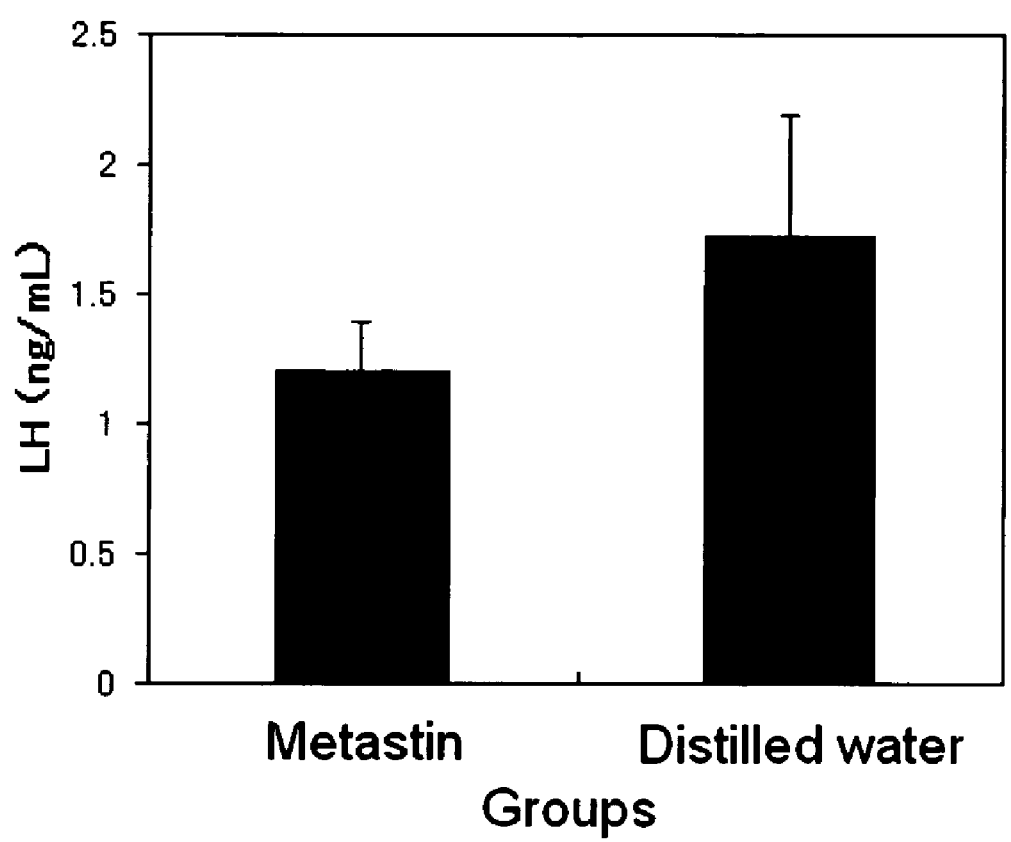
FIG. 10 shows LH level in rat plasma after sustained administration of human metastin.
Figure 11:
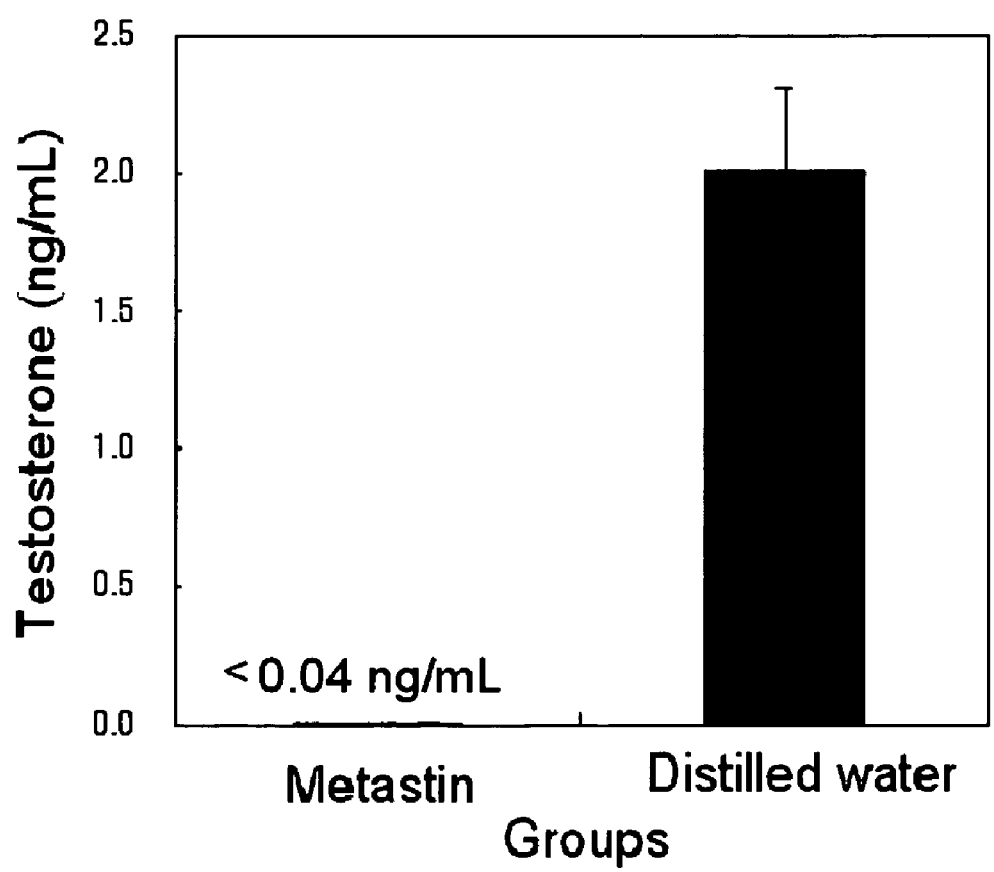
FIG. 11 shows testosterone level in rat plasma after sustained administration of human metastin.

The levels of FSH, LH and testosterone in rat plasma after the sustained administration of human metastin are shown in FIG. 9, FIG. 10 and FIG. 11, respectively. It is noted that FSH and testosterone significantly decreased after the sustained administration of human metastin. With regard to LH, any significant change was not detectable.

Figure 12:
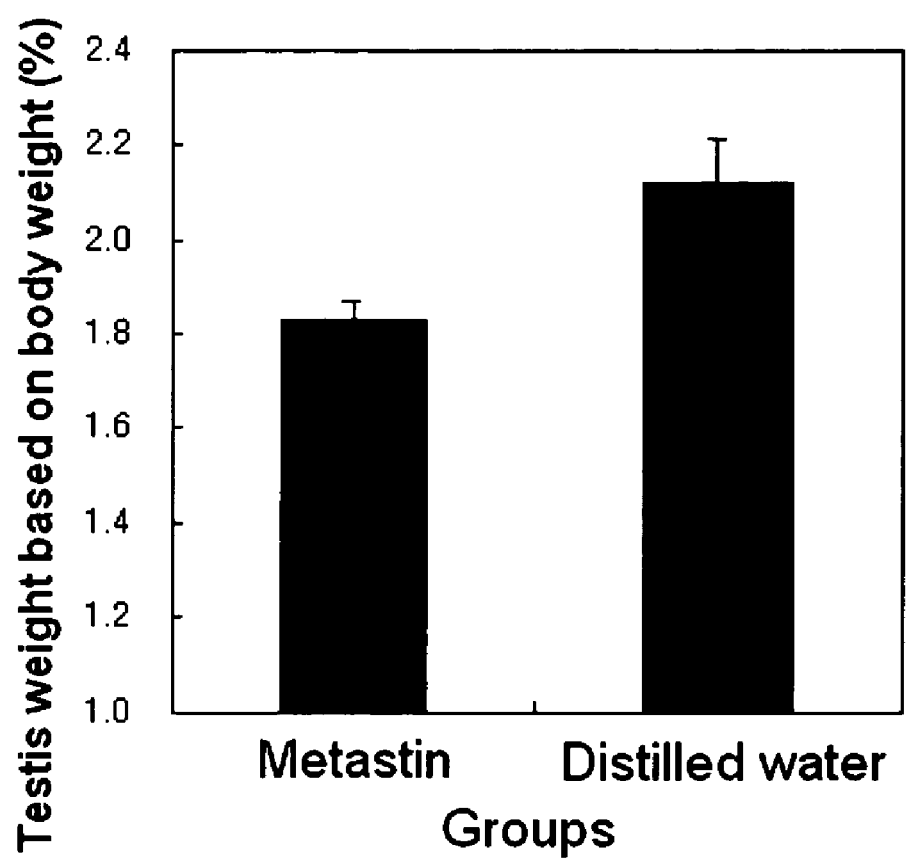
FIG. 12 shows rat testis weight (percentage (%) based on its body weight) after sustained administration of human metastin.

The weight of rat testis (percentage % based on the body weight) after the sustained administration of human metastin is shown in FIG. 12. It is noted that the weight of testis significantly decreased after the sustained administration of human metastin.

The foregoing results reveal that the release of gonadotropins and the production of testosterone in the testis were reduced by sustained administration of human metastin. In general, reduction in the stimulation of testosterone production results in reduction in the testis weight. It is considered that the reduction in the testis weight by the sustained administration of human metastin in this EXAMPLE reflects the reduction in the stimulation of testosterone production.

PREPARATION EXAMPLE 1

| (1) | Human metastin | 5.0 mg |
|---|---|---|
| (2) | Sodium chloride | 20.0 mg |
| (3) | Distilled water | To make the whole volume 2 ml. |

After 5.0 mg of human metastin and 20.0 mg of sodium chloride are dissolved in distilled water, water is added to the solution to make the whole volume 2 ml. The solution is filtrated and the filtrate is filled up in an ampoule of 2 ml under sterile conditions. The ampoule is sterilized and sealed to give a solution for injection.

INDUSTRIAL APPLICABILITY

The polypeptide and receptors of the present invention, the DNA of the present invention, etc. are useful for screening for, e.g., gonadal function improving agents, agents for preventing/treating sterility, ovulation inducers or promoters, gonadotropic hormone secretion promoters, gonadotropic hormone secretion inhibitors, sex hormone secretion promoters, sex hormone secretion inhibitors, etc.

The polypeptide and receptors of the present invention, the DNA of the present invention, and the compound or its salts that promote the function/activity of the polypeptide or receptors of the present invention possess an excellent gonadotropic hormone secretion promoting activity, gonadotropic hormone secretion inhibiting activity, sex hormone secretion promoting activity, sex hormone secretion inhibiting activity, ovulation inducing or promoting activity, etc. and are useful as low toxic and safe, e.g., gonadal function improving agents, agents for preventing/treating sterility, ovulation inducers or promoters, gonadotropic hormone secretion promoters or sex hormone secretion promoters, etc. In addition, the polypeptide and receptors of the present invention, the DNA of the present invention and the compound or its salts that promote the function/activity of the polypeptide or receptors of the present invention are useful as gonadotropic hormone secretion inhibitors, sex hormone secretion inhibitors, agents for preventing/treating hormone-sensitive cancers or endometriosis, ovarian follicular maturation inhibitors, menstrual cycle-suspending agents, etc., either by administering these agents in an effective dose sufficient to inhibit the secretion of gonadotropic hormone or sex hormone (e.g., by continuous administration, sustained administration, etc.), or by retaining these agents in a mammal at the site or tissue where the pharmaceutical effects are to be exhibited, at a level more than required. The compound or its salts that inhibit the function/activity of the polypeptide or receptors of the present invention are usable as ovulation inhibitors, ovarian function regulators, etc. and can be used as contraceptives or agents for preventing/treating precocious puberty, hormone-sensitive cancers, endometriosis, etc.

The invention claimed is:

1. A method of inhibiting secretion of follicle-stimulating hormone and testosterone in a male mammal, comprising continuously administering to said male mammal an effective dose of a polypeptide comprising the amino acid sequence selected from the group consisting of SEQ ID NO: 1, SEQ ID NO: 2, SEQ ID NO: 11, SEQ ID NO: 13, and SEQ ID NO: 15.

2. The method of claim 1, wherein the polypeptide is administered parenterally.

* * * * *

SEQUENCE LISTING

```
<160> NUMBER OF SEQ ID NOS: 25

<210> SEQ ID NO 1
<211> LENGTH: 10
<212> TYPE: PRT
<213> ORGANISM: Artificial Sequence
<220> FEATURE:
<223> OTHER INFORMATION: synthetic peptide derived from human metastin
      (45-54), wherein the C-terminus is amide (-CONH2) form

<400> SEQUENCE: 1

Tyr Asn Trp Asn Ser Phe Gly Leu Arg Phe
                5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic peptide derived from mouse metastin
      (43-52) and rat metastin (43-52), wherein the C-terminus is amide
      (-CONH2) form

<400> SEQUENCE: 2

Tyr Asn Trp Asn Ser Phe Gly Leu Arg Tyr
                5                   10

<210> SEQ ID NO 3
<211> LENGTH: 54
<212> TYPE: PRT
```

<213> ORGANISM: Homo sapiens
<220> FEATURE:
<223> OTHER INFORMATION: the C-terminus of the polypeptide is amide
      (-CONH2) form

<400> SEQUENCE: 3

Gly Thr Ser Leu Ser Pro Pro Glu Ser Ser Gly Ser Arg Gln Gln
                 5                  10                  15

Pro Gly Leu Ser Ala Pro His Ser Arg Gln Ile Pro Ala Pro Gln Gly
             20                  25                  30

Ala Val Leu Val Gln Arg Glu Lys Asp Leu Pro Asn Tyr Asn Trp Asn
         35                  40                  45

Ser Phe Gly Leu Arg Phe
     50

<210> SEQ ID NO 4
<211> LENGTH: 162
<212> TYPE: DNA
<213> ORGANISM: Homo sapiens

<400> SEQUENCE: 4
gggacctcgc tgtccccgcc ccccgagagc tccgggagcc gccagcagcc gggcctgtcc      60
gccccccaca gccgccagat ccccgcaccc cagggcgcgg tgctggtgca gcgggagaag     120
gacctgccga actacaactg gaactccttc ggcctgcgct tc                         162

<210> SEQ ID NO 5
<211> LENGTH: 52
<212> TYPE: PRT
<213> ORGANISM: Mus musculus

<400> SEQUENCE: 5

Ser Ser Pro Cys Pro Pro Val Glu Gly Pro Ala Gly Arg Gln Arg Pro
                 5                  10                  15

Leu Cys Ala Ser Arg Ser Arg Leu Ile Pro Ala Pro Arg Gly Ala Val
             20                  25                  30

Leu Val Gln Arg Glu Lys Asp Leu Ser Thr Tyr Asn Trp Asn Ser Phe
         35                  40                  45

Gly Leu Arg Tyr
     50

<210> SEQ ID NO 6
<211> LENGTH: 156
<212> TYPE: DNA
<213> ORGANISM: Mus musculus

<400> SEQUENCE: 6
tcgtcgccat gccgccggt tgagggcccc gcggggcgcc agcggcccct gtgtgcctcc      60
cgcagtcgcc tgatccctgc gccccgcgga gcggtgctgg tgcagcggga agaggacctg    120
tccacctaca actggaactc cttcggcctg cgctac                              156

<210> SEQ ID NO 7
<211> LENGTH: 52
<212> TYPE: PRT
<213> ORGANISM: Rattus norvegicus

<400> SEQUENCE: 7

Thr Ser Pro Cys Pro Pro Val Glu Asn Pro Thr Gly His Gln Arg Pro
                 5                  10                  15

Pro Cys Ala Thr Arg Ser Arg Leu Ile Pro Ala Pro Arg Gly Ser Val

-continued

```
                20                  25                  30
Leu Val Gln Arg Glu Lys Asp Met Ser Ala Tyr Asn Trp Asn Ser Phe
        35                  40                  45

Gly Leu Arg Tyr
    50
```

<210> SEQ ID NO 8
<211> LENGTH: 156
<212> TYPE: DNA
<213> ORGANISM: Rattus norvegicus

<400> SEQUENCE: 8

```
acatcgccat gcccgccggt ggagaacccc acggggcacc agcggccccc gtgtgccacc        60
cgcagtcgcc tgatccctgc ccccgcgga tcggtgctgg tgcagcgcga aaggacatg         120 tcagcctaca actggaactc ctttggcctg cgctac                                 156
```

<210> SEQ ID NO 9
<211> LENGTH: 15
<212> TYPE: PRT
<213> ORGANISM: Artificial Sequence
<220> FEATURE:
<223> OTHER INFORMATION: synthetic peptide derived from human metastin
      (40-54), wherein the C-terminus of the polypeptide is amide
      (-CONH2) form

<400> SEQUENCE: 9

```
Lys Asp Leu Pro Asn Tyr Asn Trp Asn Ser Phe Gly Leu Arg Phe
                5                  10                  15
```

<210> SEQ ID NO 10
<211> LENGTH: 45
<212> TYPE: DNA
<213> ORGANISM: Artificial Sequence
<220> FEATURE:
<223> OTHER INFORMATION: the base sequence of DNA encoding human
      metastin (40-54)

<400> SEQUENCE: 10

```
aaggacctgc cgaactacaa ctggaactcc ttcggcctgc gcttc                       45
```

<210> SEQ ID NO 11
<211> LENGTH: 9
<212> TYPE: PRT
<213> ORGANISM: Artificial Sequence
<220> FEATURE:
<223> OTHER INFORMATION: synthetic peptide derived from human metastin
      (46-54), wherein the C-terminus of the polypeptide is amide
      (-CONH2) form

<400> SEQUENCE: 11

```
Asn Trp Asn Ser Phe Gly Leu Arg Phe
                5
```

<210> SEQ ID NO 12
<211> LENGTH: 27
<212> TYPE: DNA
<213> ORGANISM: Artificial Sequence
<220> FEATURE:
<223> OTHER INFORMATION: the base sequence of DNA encoding human
      metastin (46-54)

<400> SEQUENCE: 12

```
aactggaact ccttcggcct gcgcttc                                           27
```

```
<210> SEQ ID NO 13
<211> LENGTH: 8
<212> TYPE: PRT
<213> ORGANISM: Artificial Sequence
<220> FEATURE:
<223> OTHER INFORMATION: synthetic peptide derived from human metastin
      (47-54), wherein the C-terminus of the polypeptide is amide
      (-CONH2) form

<400> SEQUENCE: 13

Trp Asn Ser Phe Gly Leu Arg Phe
                5

<210> SEQ ID NO 14
<211> LENGTH: 24
<212> TYPE: DNA
<213> ORGANISM: Artificial Sequence
<220> FEATURE:
<223> OTHER INFORMATION: the base sequence of DNA encoding human
      metastin (47-54)

<400> SEQUENCE: 14
tggaactcct tcggcctgcg cttc                                          24

<210> SEQ ID NO 15
<211> LENGTH: 7
<212> TYPE: PRT
<213> ORGANISM: Artificial Sequence
<220> FEATURE:
<223> OTHER INFORMATION: synthetic peptide derived from human metastin
      (48-54), wherein the C-terminus of the polypeptide is amide
      (-CONH2) form

<400> SEQUENCE: 15

Asn Ser Phe Gly Leu Arg Phe
            5

<210> SEQ ID NO 16
<211> LENGTH: 21
<212> TYPE: DNA
<213> ORGANISM: Artificial Sequence
<220> FEATURE:
<223> OTHER INFORMATION: the base sequence of DNA encoding human metastin (48-54)

<400> SEQUENCE: 16
aactccttcg gcctgcgctt c                                             21

<210> SEQ ID NO 17
<211> LENGTH: 30
<212> TYPE: DNA
<213> ORGANISM: Artificial Sequence
<220> FEATURE:
<223> OTHER INFORMATION: the base sequence of DNA encoding human metastin (45-54)

<400> SEQUENCE: 17
tacaactgga actccttcgg cctgcgcttc                                    30

<210> SEQ ID NO 18
<211> LENGTH: 30
<212> TYPE: DNA
<213> ORGANISM: Artificial Sequence
<220> FEATURE:
<223> OTHER INFORMATION: the base sequence of DNA encoding mouse metastin (43-52)

<400> SEQUENCE: 18
tacaactgga actccttcgg cctgcgctac                                    30
```

<210> SEQ ID NO 19
<211> LENGTH: 30
<212> TYPE: DNA
<213> ORGANISM: Artificial Sequence
<220> FEATURE:
<223> OTHER INFORMATION: the base sequence of DNA encoding rat metastin (43-52)

<400> SEQUENCE: 19
tacaactgga actcctttgg cctgcgctac                                    30

<210> SEQ ID NO 20
<211> LENGTH: 398
<212> TYPE: PRT
<213> ORGANISM: Homo sapiens

<400> SEQUENCE: 20

Met His Thr Val Ala Thr Ser Gly Pro Asn Ala Ser Trp Gly Ala Pro
 1               5                  10                  15

Ala Asn Ala Ser Gly Cys Pro Gly Cys Gly Ala Asn Ala Ser Asp Gly
             20                  25                  30

Pro Val Pro Ser Pro Arg Ala Val Asp Ala Trp Leu Val Pro Leu Phe
         35                  40                  45

Phe Ala Ala Leu Met Leu Leu Gly Leu Val Gly Asn Ser Leu Val Ile
     50                  55                  60

Tyr Val Ile Cys Arg His Lys Pro Met Arg Thr Val Thr Asn Phe Tyr
 65                  70                  75                  80

Ile Ala Asn Leu Ala Ala Thr Asp Val Thr Phe Leu Leu Cys Cys Val
                 85                  90                  95

Pro Phe Thr Ala Leu Leu Tyr Pro Leu Pro Gly Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Ala Val Ser Leu Ser Ile Trp Val Gly Ser Ala Val Ser Ala Pro
                165                 170                 175

Val Leu Ala Leu His Arg Leu Ser Pro Gly Pro Arg Ala Tyr Cys Ser
            180                 185                 190

Glu Ala Phe Pro Ser Arg Ala Leu Glu Arg Ala Phe Ala Leu Tyr Asn
        195                 200                 205

Leu Leu Ala Leu Tyr Leu Leu Pro Leu Leu Ala Thr Cys Ala Cys Tyr
    210                 215                 220

Ala Ala Met Leu Arg His Leu Gly Arg Val Ala Val Arg Pro Ala Pro
225                 230                 235                 240

Ala Asp Ser Ala Leu Gln Gly Gln Val Leu Ala Glu Arg Ala Gly Ala
                245                 250                 255

Val Arg Ala Lys Val Ser Arg Leu Val Ala Val Val Leu Leu Phe
            260                 265                 270

Ala Ala Cys Trp Gly Pro Ile Gln Leu Phe Leu Val Leu Gln Ala Leu
        275                 280                 285

Gly Pro Ala Gly Ser Trp His Pro Arg Ser Tyr Ala Ala Tyr Ala Leu
    290                 295                 300

Lys Thr Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Arg Arg
            325                 330                 335

Val Cys Pro Cys Ala Pro Arg Arg Pro Arg Arg Pro Arg Arg Pro Gly
            340                 345                 350

Pro Ser Asp Pro Ala Ala Pro His Ala Glu Leu His Arg Leu Gly Ser
            355                 360                 365

His Pro Ala Pro Ala Arg Ala Gln Lys Pro Gly Ser Ser Gly Leu Ala
        370                 375                 380

Ala Arg Gly Leu Cys Val Leu Gly Glu Asp Asn Ala Pro Leu
385                 390                 395     398

<210> SEQ ID NO 21
<211> LENGTH: 1194
<212> TYPE: DNA
<213> ORGANISM: Homo sapiens

<400> SEQUENCE: 21

| | | |
|---|---|---|
| atgcacaccg tggctacgtc cggacccaac gcgtcctggg gggcaccggc caacgcctcc | 60 |
| ggctgcccgg ctgtggcgc caacgcctcg gacggcccag tcccttcgcc gcgggccgtg | 120 |
| gacgcctggc tcgtgccgct cttcttcgcg gcgctgatgc tgctgggcct ggtggggaac | 180 |
| tcgctggtca tctacgtcat ctgccgccac aagccgatgc ggaccgtgac caacttctac | 240 |
| atcgccaacc tggcggccac ggacgtgacc ttcctcctgt gctgcgtccc cttcacggcc | 300 |
| ctgctgtacc cgctgccggc tgggtgctg gcgacttca tgtgcaagtt cgtcaactac | 360 |
| atccagcagg tctcggtgca ggccacgtgt gccactctga ccgccatgag tgtggaccgc | 420 |
| tggtacgtga cggtgttccc gttgcgcgcc ctgcaccgcc gcacgccccg cctggcgctg | 480 |
| gctgtcagcc tcagcatctg gtaggctct cggcggtgt ctgcgccggt gctcgccctg | 540 |
| caccgcctgt cacccgggcc gcgcgcctac tgcagtgagg ccttccccag ccgcgccctg | 600 |
| gagcgcgcct tcgcactgta caacctgctg gcgctgtacc tgctgccgct gctcgccacc | 660 |
| tgcgcctgct atgcggccat gctgcgccac ctgggccggg tcgccgtgcg ccccgcgccc | 720 |
| gccgatagcg ccctgcaggg gcaggtgctg gcagagcgcg caggcgccgt gcgggccaag | 780 |
| gtctcgcggc tggtggcggc cgtggtcctg ctcttcgccg cctgctgggg ccccatccag | 840 |
| ctgttcctgg tgctgcaggc gctgggcccc gcgggctcct ggcacccacg cagctacgcc | 900 |
| gcctacgcgc ttaagacctg gctcactgc atgtcctaca gcaactccgc gctgaacccg | 960 |
| ctgctctacg cctttcctgggg ctcgcacttc cgacaggcct ccgccgcgt ctgccccctgc | 1020 |
| gcgccgcgcc gccccgccg ccccgccgg cccggaccct cggacccgc agccccacac | 1080 |
| gcggagctgc accgcctggg gtcccaccg gccccgcca gggcgcagaa gccagggagc | 1140 |
| agtgggctgg ccgcgcgcgg gctgtgcgtc ctggggggagg acaacgcccc tctc | 1194 |

<210> SEQ ID NO 22
<211> LENGTH: 396
<212> TYPE: PRT
<213> ORGANISM: Rattus norvegicus

<400> SEQUENCE: 22

Met Ala Ala Glu Ala Thr Leu Gly Pro Asn Val Ser Trp Trp Ala Pro
                5                   10                  15

Ser Asn Ala Ser Gly Cys Pro Gly Cys Gly Val Asn Ala Ser Asp Gly
            20                  25                  30

Pro Gly Ser Ala Pro Arg Pro Leu Asp Ala Trp Leu Val Pro Leu Phe
        35                  40                  45

```
Phe Ala Ala Leu Met Leu Leu Gly Leu Val Gly Asn Ser Leu Val Ile
         50                  55                  60

Phe Val Ile Cys Arg His Lys His Met Gln Thr Val Thr Asn Phe Tyr
 65                  70                  75                  80

Ile Ala Asn Leu Ala Ala Thr Asp Val Thr Phe Leu Leu Cys Cys Val
                 85                  90                  95

Pro Phe Thr Ala Leu Leu Tyr Pro Leu Pro Thr Trp Val Leu Gly Asp
                100                 105                 110

Phe Met Cys Lys Phe Val Asn Tyr Ile Gln Gln Val Ser Val Gln Ala
                115                 120                 125

Thr Cys Ala Thr Leu Thr Ala Met Ser Val Asp Arg Trp Tyr Val Thr
            130                 135                 140

Val Phe Pro Leu Arg Ala Leu His Arg Arg Thr Pro Arg Leu Ala Leu
145                 150                 155                 160

Thr Val Ser Leu Ser Ile Trp Val Gly Ser Ala Ala Val Ser Ala Pro
                165                 170                 175

Val Leu Ala Leu His Arg Leu Ser Pro Gly Pro His Thr Tyr Cys Ser
                180                 185                 190

Glu Ala Phe Pro Ser Arg Ala Leu Glu Arg Ala Phe Ala Leu Tyr Asn
            195                 200                 205

Leu Leu Ala Leu Tyr Leu Leu Pro Leu Leu Ala Thr Cys Ala Cys Tyr
210                 215                 220

Gly Ala Met Leu Arg His Leu Gly Arg Ala Ala Val Arg Pro Ala Pro
225                 230                 235                 240

Thr Asp Gly Ala Leu Gln Gly Gln Leu Leu Ala Gln Arg Ala Gly Ala
                245                 250                 255

Val Arg Thr Lys Val Ser Arg Leu Val Ala Ala Val Leu Leu Phe
                260                 265                 270

Ala Ala Cys Trp Gly Pro Ile Gln Leu Phe Leu Val Leu Gln Ala Leu
            275                 280                 285

Gly Pro Ser Gly Ala Trp His Pro Arg Ser Tyr Ala Ala Tyr Ala Leu
290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
                325                 330                 335

Val Cys Pro Cys Gly Pro Gln Arg Gln Arg Arg Pro His Ala Ser Ala
                340                 345                 350

His Ser Asp Arg Ala Ala Pro His Ser Val Pro His Ser Arg Ala Ala
            355                 360                 365

His Pro Val Arg Val Arg Thr Pro Glu Pro Gly Asn Pro Val Val Arg
            370                 375                 380

Ser Pro Ser Val Gln Asp Glu His Thr Ala Pro Leu
385                 390                 395

<210> SEQ ID NO 23
<211> LENGTH: 1188
<212> TYPE: DNA
<213> ORGANISM: Rattus norvegicus

<400> SEQUENCE: 23
atggccgcag aggcgacgtt gggtccgaac gtgagctggt gggctccgtc caacgcttcg     60
ggatgcccgg gctgcggtgt caatgcctcg gatggcccag ctccgcgcc aaggcccctg    120
```

-continued

```
gatgcctggc tggtgcccct gttttccgct gccctaatgt tgctggggct agtcgggaac        180
tcactggtca tcttcgttat ctgccgccac aagcacatgc agaccgtcac caatttctac        240
atcgctaacc tggcggccac agatgtcact ttccttctgt gctgcgtacc cttcaccgcg        300
ctcctctatc cgctgccac  ctgggtgctg ggagacttca tgtgcaaatt cgtcaactac        360
atccagcagg tctcggtgca agccacatgt gccactttga cagccatgag tgtggaccgc        420
tggtacgtga ctgtgttccc gctgcgtgca cttcaccgcc gcactccgcg cctggccctg        480
actgtcagcc ttagcatctg ggtgggttcc gcagctgttt ccgccccggt gctggctctg        540
caccgcctgt cgcccgggcc tcacacctac tgcagtgagg cgtttcccag ccgtgccctg        600
gagcgcgctt cgcgctcta  caacctgctg gccctatacc tgctgccgct gctcgccacc        660
tgcgcctgct acggtgccat gctgcgccac ctgggccgcg ccgctgtacg ccccgcaccc        720
actgatggcg ccctgcaggg gcagctgcta gcacagcgcg ctggagcagt gcgcaccaag        780
gtctcccggc tggtggccgc tgtcgtcctg ctcttcgccg cctgctgggg cccgatccag        840
ctgttcctgg tgcttcaagc cctgggcccc tcggggggcct ggcaccctcg aagctatgcc       900
gcctacgcgc tcaagatctg ggctcactgc atgtcctaca gcaattctgc gctcaacccg        960
ctgctctatg ccttcctggg ttcccacttc agacaggcct tctgccgcgt gtgcccctgc       1020
ggcccgcaac gccagcgtcg gccccacgcg tcagcgcact cggaccgagc cgcacccat        1080
agtgtgccgc acagccgggc tgcgcacccct gtccgggtca ggaccccga  gcctgggaac      1140
cctgtggtgc gctcgccctc tgttcaggat gaacacactg ccccactc              1188
```

<210> SEQ ID NO 24
<211> LENGTH: 396
<212> TYPE: PRT
<213> ORGANISM: Mus musculus

<400> SEQUENCE: 24

```
Met Ala Thr Glu Ala Thr Leu Ala Pro Asn Val Thr Trp Trp Ala Pro
  1               5                  10                  15

Ser Asn Ala Ser Gly Cys Pro Gly Cys Gly Val Asn Ala Ser Asp Asp
             20                  25                  30

Pro Gly Ser Ala Pro Arg Pro Leu Asp Ala Trp Leu Val Pro Leu Phe
         35                  40                  45

Phe Ala Thr Leu Met Leu Leu Gly Leu Val Gly Asn Ser Leu Val Ile
     50                  55                  60

Tyr Val Ile Cys Arg His Lys His Met Gln Thr Val Thr Asn Phe Tyr
 65                  70                  75                  80

Ile Ala Asn Leu Ala Ala Thr Asp Val Thr Phe Leu Leu Cys Cys Val
                 85                  90                  95

Pro Phe Thr Ala Leu Leu Tyr Pro Leu Pro Ala Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Ala Val Ser Leu Ser Ile Trp Val Gly Ser Ala Ala Val Ser Ala Pro
                165                 170                 175

Val Leu Ala Leu His Arg Leu Ser Pro Gly Pro Arg Thr Tyr Cys Ser
            180                 185                 190
```

Glu Ala Phe Pro Ser Arg Ala Leu Glu Arg Ala Phe Ala Leu Tyr Asn
                195                 200                 205

Leu Leu Ala Leu Tyr Leu Leu Pro Leu Leu Ala Thr Cys Ala Cys Tyr
            210                 215                 220

Gly Ala Met Leu Arg His Leu Gly Arg Ala Ala Val Arg Pro Ala Pro
225                 230                 235                 240

Thr Asp Gly Ala Leu Gln Gly Gln Leu Leu Ala Gln Arg Ala Gly Ala
                245                 250                 255

Val Arg Thr Lys Val Ser Arg Leu Val Ala Ala Val Leu Leu Phe
                260                 265                 270

Ala Ala Cys Trp Gly Pro Ile Gln Leu Phe Leu Val Leu Gln Ala Leu
            275                 280                 285

Gly Pro Ser Gly Ala Trp His Pro Arg Ser Tyr Ala Ala Tyr Ala Val
            290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
                325                 330                 335

Val Cys Pro Cys Cys Arg Gln Arg Gln Arg Arg Pro His Thr Ser Ala
                340                 345                 350

His Ser Asp Arg Ala Ala Thr His Thr Val Pro His Ser Arg Ala Ala
            355                 360                 365

His Pro Val Arg Ile Arg Ser Pro Glu Pro Gly Asn Pro Val Val Arg
370                 375                 380

Ser Pro Cys Ala Gln Ser Glu Arg Thr Ala Ser Leu
385                 390                 395

<210> SEQ ID NO 25
<211> LENGTH: 1188
<212> TYPE: DNA
<213> ORGANISM: Mus musculus

<400> SEQUENCE: 25
atggccaccg aggcgacatt ggctcccaat gtgacctggt gggctccgtc caacgcttca      60
ggatgcccag ctgcggtgt caacgcctcg gatgacccag ctctgcgcc aaggcccctg      120 gatgcctggc tggttcccct gttttcgct acactcatgt tgcttgggct ggtcggaaac      180
tcattggtca tctacgttat ctgccgccac aagcacatgc agacagttac caacttctac      240
atcgctaacc tggctgccac agacgtcact ttcctactgt gctgcgtgcc cttcaccgca      300
ctcctctacc cgctgccgc ctgggtgctg ggagacttca tgtgcaaatt cgtcaactac      360
atccagcagg tctcggtgca agccacatgt gccactctga cggccatgag tgtggaccgc      420
tggtatgtga ctgtgttccc gctgcgtgca cttcaccgcc gcactccgcg cctggccctg      480
gctgtcagcc tcagcatctg ggtggggtca gcagctgtgt ccgccccggt gctggccctg      540
caccgcctgt cgccagggcc tcgcacctac tgcagcgagg cgtttcccag ccgcgccctg      600
gagcgcgcct tcgcgctcta caacctgctg gctctatatc tgctgccgct gctcgccacc      660
tgcgcctgct acggcgccat gctgcgccac ctgggccgtg cggctgtacg ccccgcaccc      720
actgacggcg ccctgcaggg acagctgcta gcacagcgcg ccggagcagt gcgcaccaag      780
gtctcccggc tggtggccgc tgtcgtcctg ctcttcgccg cctgctgggg cccgatccag      840
ctgttcctgg tgcttcaagc cctgggcccc tcgggggcct ggcaccctcg aagctatgcc      900
gcctacgcgg tcaagatctg ggctcactgc atgtcctaca gcaactcggc gctcaatccg      960

-continued

```
ctgctctatg ccttcctggg ttcacacttc agacaggcct tctgccgcgt gtgcccctgc    1020
tgccggcaac gccagcgccg gccccacacg tcagcgcact cggaccgagc tgcaactcac    1080
actgtgccgc acagccgtgc tgcgcaccct gtgcggatca ggagcccgga gcctgggaac    1140
cctgtggtgc gctcgccctg cgctcagagt gaacgcactg cctcactc                1188
```